US011478438B2

(12) United States Patent
Zhang et al.

(10) Patent No.: US 11,478,438 B2
(45) Date of Patent: Oct. 25, 2022

(54) NECROSIS INHIBITORS

(71) Applicant: National Institute of Biological Sciences, Beijing, Beijing (CN)

(72) Inventors: Zhiyuan Zhang, Beijing (CN); Xiaodong Wang, Beijing (CN); Yaning Su, Beijing (CN); Hanying Ruan, Beijing (CN); Yan Ren, Beijing (CN)

(73) Assignee: National Institute of Biological Sciences, Beijing, Beijing (CN)

( * ) Notice: Subject to any disclaimer, the term of this patent is extended or adjusted under 35 U.S.C. 154(b) by 486 days.

(21) Appl. No.: 16/787,052

(22) Filed: Feb. 11, 2020

(65) Prior Publication Data

US 2020/0182617 A1 Jun. 11, 2020

Related U.S. Application Data

(63) Continuation of application No. 16/143,706, filed on Sep. 27, 2018, now Pat. No. 11,105,631, which is a
(Continued)

(51) Int. Cl.
| | |
|---|---|
| A61K 31/165 | (2006.01) |
| A61K 31/10 | (2006.01) |
| A61K 31/167 | (2006.01) |
| C07C 233/01 | (2006.01) |
| C07C 235/38 | (2006.01) |
| C07D 231/02 | (2006.01) |
| C07D 263/04 | (2006.01) |
| C07D 205/04 | (2006.01) |
| C07D 265/30 | (2006.01) |
| C07D 207/12 | (2006.01) |
| C07D 211/70 | (2006.01) |
| C07D 231/04 | (2006.01) |
| C07D 231/08 | (2006.01) |
| C07D 233/38 | (2006.01) |
| C07D 405/04 | (2006.01) |
| C07D 409/04 | (2006.01) |
| C07D 241/04 | (2006.01) |
| C07D 417/04 | (2006.01) |
| C07D 261/02 | (2006.01) |
| C07D 263/22 | (2006.01) |
| C07D 203/18 | (2006.01) |
| C07D 205/08 | (2006.01) |

(Continued)

(52) U.S. Cl.
CPC .......... *A61K 31/165* (2013.01); *A61K 31/10* (2013.01); *A61K 31/167* (2013.01); *C07C 233/01* (2013.01); *C07C 235/38* (2013.01); *C07D 203/18* (2013.01); *C07D 205/04* (2013.01); *C07D 205/08* (2013.01); *C07D 207/06* (2013.01); *C07D 207/08* (2013.01); *C07D 207/12* (2013.01); *C07D 207/20* (2013.01); *C07D 207/24* (2013.01); *C07D 207/27* (2013.01); *C07D 207/333* (2013.01); *C07D 211/16* (2013.01); *C07D 211/70* (2013.01); *C07D 211/82* (2013.01); *C07D 231/02* (2013.01); *C07D 231/04* (2013.01); *C07D 231/08* (2013.01); *C07D 233/38* (2013.01); *C07D 241/04* (2013.01); *C07D 261/02* (2013.01); *C07D 263/04* (2013.01); *C07D 263/22* (2013.01); *C07D 265/30* (2013.01); *C07D 405/04* (2013.01); *C07D 409/04* (2013.01); *C07D 417/04* (2013.01); *G01C 19/5649* (2013.01); *G01C 19/5747* (2013.01)

(58) Field of Classification Search
CPC .... A61K 31/165; A61K 31/167; A61K 31/10; C07C 233/01; C07C 235/38; G01C 19/5649; G01C 19/5747; C07D 263/04; C07D 205/04; C07D 265/30; C07D 207/12; C07D 211/70; C07D 231/04; C07D 231/08; C07D 233/38; C07D 405/04; C07D 409/04; C07D 241/04; C07D 417/04; C07D 261/02; C07D 263/22; C07D 203/18; C07D 205/08; C07D 207/06; C07D 207/08; C07D 207/20; C07D 207/234; C07D 207/27; C07D 207/333; C07D 211/16; C07D 211/82; C07D 231/02
See application file for complete search history.

(56) References Cited

U.S. PATENT DOCUMENTS 6,756,394 B1 6/2004 Yuan et al.
8,278,344 B2 10/2012 Cuny et al.
(Continued)

FOREIGN PATENT DOCUMENTS

WO 2009023272 2/2009
WO 2010075290 7/2010
(Continued)

OTHER PUBLICATIONS

International Search Report & Written Opinion PCT/CN2015/098385.
Extended European Search Report EP No. 15871955.9.

*Primary Examiner* — Erich A Leeser
(74) *Attorney, Agent, or Firm* — Richard Aron Osman

(57) ABSTRACT

The invention provides amides that inhibit cellular necrosis and/or human receptor interacting protein 1 kinase (RIP1), including corresponding sulfonamides, and pharmaceutically acceptable salts, hydrates and stereoisomers thereof. The compounds are employed in pharmaceutical compositions, and methods of making and use, including treating a person in need thereof with an effective amount of the compound or composition, and detecting a resultant improvement in the person's health or condition.

22 Claims, No Drawings

Related U.S. Application Data continuation of application No. 15/632,422, filed on Jun. 26, 2017, now Pat. No. 10,092,529, which is a continuation of application No. PCT/CN2015/098385, filed on Dec. 23, 2015, which is a continuation of application No. PCT/CN2014/094734, filed on Dec. 24, 2014.

(51) Int. Cl.

| | | |
|---|---|---|
| *C07D 207/06* | (2006.01) | |
| *C07D 207/08* | (2006.01) | |
| *C07D 207/20* | (2006.01) | |
| *C07D 207/24* | (2006.01) | |
| *C07D 207/27* | (2006.01) | |
| *C07D 207/333* | (2006.01) | |
| *C07D 211/16* | (2006.01) | |
| *C07D 211/82* | (2006.01) | |
| *G01C 19/5649* | (2012.01) | |
| *G01C 19/5747* | (2012.01) | |

(56) References Cited

U.S. PATENT DOCUMENTS

| | | |
|---|---|---|
| 2003/0083386 A1 | 5/2003 | Tuan et al. |
| 2009/0099242 A1 | 4/2009 | Cuny et al. |
| 2011/0144169 A1 | 6/2011 | Cuny et al. |
| 2012/0122889 A1 | 5/2012 | Yuan et al. |
| 2012/0309795 A1 | 12/2012 | Cuny et al. |
| 2013/0317701 A1 | 11/2013 | Ooyabu et al. |

FOREIGN PATENT DOCUMENTS

| | | | | |
|---|---|---|---|---|
| WO | WO 2010/075561 | * | 7/2010 | ............. A01N 43/40 |
| WO | 2012125544 | | 9/2012 | |
| WO | 2014140704 | | 9/2014 | |
| WO | 2016185423 | | 11/2016 | |

* cited by examiner

NECROSIS INHIBITORS

INTRODUCTION

Tumor necrosis factor alpha (TNF-α)-induced NF-κB activation plays a central role in the immune system and inflammatory responses. Receptor-interacting protein 1 (RIP1) is a multi-functional signal transducer involved in mediating nuclear factor κB (NF-κB) activation, apoptosis, and necroptosis. The kinase activity of RIP1 is critically involved in mediating necroptosis, a caspase-independent pathway of necrotic cell death. Holler et al. Nat Immunol 2000; 1: 489-495; Degterev et al. Nat Chem Biol 2008; 4: 313-321.

Necroptosis plays a role in various pathological forms of cell death, including ischemic brain injury, neurodegenerative diseases and viral infections. Dunai, et al., Dec 2011, Pathol. Oncol. Res.: POR 17 (4): 791-800. Necrostatin-1 (Nec-1), a small molecule inhibitor of RIP1 kinase activity, can block necroptosis. Degterev et al. Nat Chem Biol 2005; 1: 112-119.

Related patent publications include: U.S. Pat. Nos. 6,756,394, 8,278,344, US2012122889, US2009099242, US2010317701, US2011144169, US20030083386, US20120309795, WO2009023272, WO2010075290, WO2010075561, WO2012125544.

SUMMARY OF THE INVENTION

The invention provides an inhibitor of cellular necrosis and/or human receptor interacting protein 1 kinase (RIP1), that is an amide compound of formula:

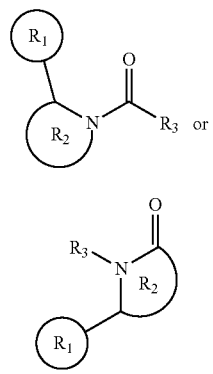

wherein:
R1 is a C3-C14 cyclic or hetero-cyclic moiety, particularly substituted or unsubstituted, 0-3 heteroatom C3-C9 cycloalkyl, cycloalkenyl, cycloalkynyl; or substituted or unsubstituted, 0-3 heteroatom C5-C14 aryl;

R2 a C3-C14 hetero-cyclic moiety, particularly substituted or unsubstituted, 1-3 heteroatom C3-C9 cycloalkyl, cycloalkenyl, cycloalkynyl; or substituted or unsubstituted, 1-3 heteroatom C5-C14 aryl; and R3 is H, substituted or unsubstituted heteroatom, substituted or unsubstituted, 0-3 heteroatom C1-C9 alkyl, alkenyl, alkynyl; or and substituted or unsubstituted, 0-3 heteroatom C5-C14 aryl, wherein each heteroatom is independently oxygen, phosphorus, sulfur or nitrogen; or a corresponding sulfonamide of the amide compound, or a pharmaceutically acceptable salt, hydrate or stereoisomer the compound or corresponding sulfonamide;

The invention also provides the corresponding sulfonamides of all the generally and specifically disclosed amides, e.g.

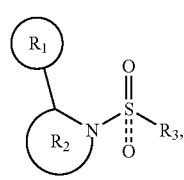

wherein S may be double bond to one or two O atoms, or a pharmaceutically acceptable salt, hydrate or stereoisomer thereof, wherein the R moieties are as described herein, or a pharmaceutically acceptable salt, hydrate or stereoisomer thereof.

The invention provides pharmaceutical compositions comprising the subject compounds, and methods of making and using the subject compounds, including methods of inhibiting cellular necrosis and/or human RIP1. The compositions may comprise a pharmaceutically-acceptable excipient, be in effective, unit dosage form, and/or comprise another, different therapeutic agents for the targeted disease or condition. In embodiments, the invention provides methods of treating a person in need thereof with an effective amount of the subject compound or pharmaceutical composition, and optionally, detecting a resultant improvement in the person's health or condition. The methods may also optionally include the antecedent step of determining that the person, particularly diagnosing and applicable disease or condition (herein).

The invention encompasses all combination of the particular embodiments recited herein.

DESCRIPTION OF PARTICULAR EMBODIMENTS OF THE INVENTION

The following descriptions of particular embodiments and examples are provided by way of illustration and not by way of limitation. Those skilled in the art will readily recognize a variety of noncritical parameters that could be changed or modified to yield essentially similar results. The invention provides myriad embodiments.

In one aspect the invention provides amide inhibitors of cellular necrosis and/or human receptor interacting protein 1 kinase (RIP1) of formula:

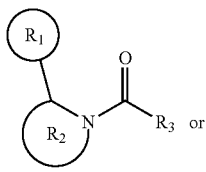

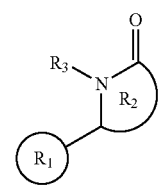

wherein:
  R₁ is a C3-C14 cyclic or hetero-cyclic moiety, particularly substituted or unsubstituted, 0-3 heteroatom C3-C9 cycloalkyl, cycloalkenyl, or cycloalkynyl; or substituted or unsubstituted, 0-3 heteroatom C5-C14 aryl;
  R₂ is a C3-C14 hetero-cyclic moiety, particularly substituted or unsubstituted, 1-3 heteroatom C3-C9 cycloalkyl, cycloalkenyl, or cycloalkynyl; or substituted or unsubstituted, 1-3 heteroatom C5-C14 aryl; and
  R₃ is H, substituted or unsubstituted heteroatom, substituted or unsubstituted, 0-3 heteroatom C1-C9 alkyl, alkenyl, or alkynyl; or and substituted or unsubstituted, 0-3 heteroatom C5-C14 aryl,
    wherein each heteroatom is independently oxygen, phosphorus, sulfur or nitrogen; or
    a corresponding sulfonamide of the amide compound, or
    a pharmaceutically acceptable salt, hydrate or stereoisomer the compound.

In particular embodiments:
  R₁ is (a) substituted or unsubstituted phenyl;
    (b) substituted or unsubstituted 2-, 3- or 4-pyridine;
    (c) substituted or unsubstituted naphthyl or 3-azanaphthyl;
    (d) substituted or unsubstituted 0-3 heteroatom cyclohexyl, cyclopentyl, such as tetrahydrofuran; or
    (e) substituted or unsubstituted 0-3 heteroatom cyclopentene or cyclopentadiene, such as pyrrole, azole (e.g. pyrazole, imidazole, triazole, tetrazole, pentazole, oxazole, isoxazole, thiazole or isothiazole), furan, dioxole thiophene, dithiole or oxathiole, preferably 2-moieties, such as 2-azole, 2-pyrrole, 2-azole (e.g. 2-pyrazole, 2-imidazole, 2-oxazole, 2-isoxazole, 2-thiozole, or 2-isothiozole), 2-furan, 2-thiophene, 2-oxole, dioxole, or 2-thiole; and/or
  R₂ is substituted or unsubstituted saturated ring with heteroatom(s):
    N, e.g. aziridine, azetidine, pyrrolidine, piperidine;
    N and O, e.g. oxazridine, oxazetidine, oxazolidine, oxazinane;
    N and S, e.g. thiaziridine, thiazetidine, thiazolidine, thiazinane;
    N and N, e.g. diaziridine, diazetidine, diazolidine (pyrazolidine), diazinane; or
  R₂ is substituted or unsubstituted unsaturated ring with heteroatom(s):
    N, e.g. pyrrole, dihydropyrrole, pyridine, dihydropyridine, tetrahydropyridine;
    N and N/S/O, e.g. azole (e.g. pyrazole, imidazole, triazole, tetrazole, pentazole, oxazole, isoxazole, thiazole or isothiazole), pyrimidine, oxazine, thiazine, triazine, ozadiazine, thiadiazine; and/or
  R₃ is substituted or unsubstituted, 0-3 heteroatom C1-C9 alkyl, alkenyl, or alkynyl, and in embodiments, R3 is fluorinated with 1, 2, 3 or 4 fluorine atoms, such as 1-dimethyl, 2-difluoropropyl.

In embodiments:
  R₁ is substituted or unsubstituted: phenyl, cyclohexyl, furan, thiophene or azole (e.g. thiazole); and/or
  R₂ is substituted or unsubstituted: aziridine, azetidine, pyrrolidine, piperidine, oxazolidine, oxazinane; diazolidine, diazinane, pyrrole, dihydropyrrole, dihydropyridine, or tetrahydropyridine; and/or
  R₃ is 1-dimethylpropyl, 1-dimethylprop-2-enyl, or 1-dimethylprop-2-ynyl, each optionally fluorinated with 1-4 F atoms.

In embodiments:
  R₁ is substituted or unsubstituted phenyl or cyclohexyl, and/or
  R₂ is substituted or unsubstituted: azetidine, pyrrolidine, piperidine, oxazolidine, diazolidine, diazinane; and/or
  R₃ is 1-dimethylpropyl; or
  a corresponding sulfonamide of the amide compound, or
  a pharmaceutically acceptable salt, hydrate or stereoisomer the compound or corresponding sulfonamide All possible combinations are encompassed as though each was expressly recited and heterocyclics include isomers, such as iso-forms.

For example, in embodiments the compound is of formula I wherein:
  R₁ is unsubstituted phenyl, and/or
  R₂ is unsubstituted: azetidine, pyrrolidine, piperidine, oxazolidine, diazolidine, diazinane; and/or
  R₃ is 1-dimethylpropyl; or
  a corresponding sulfonamide of the amide compound, or
  a pharmaceutically acceptable salt, hydrate or stereoisomer the compound or corresponding sulfonamide For example, in embodiments the compound is of formula I wherein:
  R₁ is unsubstituted phenyl, and
  R₂ is unsubstituted: azetidine, pyrrolidine, piperidine, oxazolidine, diazolidine, diazinane; and
  R₃ is 1-dimethylpropyl; or
  a corresponding sulfonamide of the amide compound, or
  a pharmaceutically acceptable salt, hydrate or stereoisomer the compound or corresponding sulfonamide In embodiments the subject compounds have a formula of Table 1.

In embodiments the invention provides pharmaceutical compositions comprising a subject compound and a pharmaceutically-acceptable excipient, in unit dosage.

In embodiments the invention provides pharmaceutical compositions comprising a subject compound and a pharmaceutically-acceptable excipient, in unit dosage, and a different therapeutic agent for a necrosis-associated disease or condition.

In embodiments the invention provides methods of treating a necrosis-associated disease or condition, comprising administering an effective amount of a subject compound or composition to a patient in need thereof.

In embodiments the invention the method of treatment comprise the antecedent step of diagnosing the necrosis-associated disease or condition, or the subsequent step of detecting a resultant amelioration of the necrosis-associated disease or condition.

Applicable diseases or conditions are necrosis—(including necroptosis) associated and include neuro-degenerative disease of the central or peripheral nervous system, endotoxic/septic shock, terminal ileitis, myocarditis, arthritis, atherosclerosis, acute enteritis, ischemic necrosis, pathology resulting from renal failure or cell death, including retinal neuronal, cardiac muscle or immune cell death, such as chemo- or radiation-induced necrosis; liver disease, including drug-induced liver damage or toxicity, acute hepatitis, etc., pancreatic disease, including necrotizing pancreatitis, heart, mesenteric, retinal, hepatic or brain/cerebral ischemic injury, nephritis, ischemic injury during reperfusion or organ storage, head trauma, including traumatic brain injury, stroke, septic shock, coronary heart disease, cardiomyopathy, myocardial infarction, bone avascular necrosis, sickle cell disease, muscle wasting, gastrointestinal disease, tuberculosis, diabetes, pathogenic alteration of blood vessels, muscular dystrophy, graft-versus-host disease, viral, bacterial and fungal infection, Crohn's disease, ulcerative colitis, asthma, etc.

Exemplary applicable viruses are human immunodeficiency virus (HIV), Epstein-Barr virus (EBV), cytomegalovirus (CMV)5 human herpesviruses (HHV), herpes simplex viruses (HSV), human T-Cell leukemia viruses (HTLV) 5 Varicella-Zoster virus (VZV), measles virus, papovaviruses (JC and BK), hepatitis viruses, adenovirus, parvoviruses, and human papillomaviruses. Exemplary diseases caused by viral infection include, but are not limited to, chicken pox, Cytomegalovirus infections, genital herpes, Hepatitis B and C, influenza, and shingles.

Exemplary applicable bacteria include, but are not limited to *Campylobacter jejuni*, *Enterobacter* species, *Enterococcus faecium*, *Enterococcus faecalis*, *Escherichia coli* (e.g., *E. coli* O157:H7), Group A streptococci, *Haemophilus influenzae*, *Helicobacter pylori*, *Listeria*, *Mycobacterium tuberculosis*, *Pseudomonas aeruginosa*, *S. pneumoniae*, *Salmonella*, *Shigella*, *Staphylococcus aureus*, and *Staphylococcus epidermidis*. Exemplary diseases caused by bacterial infection include, but are not limited to, anthrax, cholera, diphtheria, foodborne illnesses, leprosy, meningitis, peptic ulcer disease, pneumonia, sepsis, tetanus, tuberculosis, typhoid fever, and urinary tract infection.

Exemplary applicable neurodegenerative diseases are Alzheimer's disease, Huntington's disease, Parkinson's disease, amyotrophic lateral sclerosis, HIV-associated dementia, cerebral ischemia, amyotropic lateral sclerosis, multiple sclerosis, Lewy body disease, Menke's disease, Wilson's disease, Creutzfeldt-Jakob disease, and Fahr disease.

Exemplary applicable muscular dystrophies or related diseases are Becker's muscular dystrophy, Duchenne muscular dystrophy, myotonic dystrophy, limb-girdle muscular dystrophy, Landouzy-Dejerine muscular dystrophy, facioscapulohumeral muscular dystrophy (Steinert's disease), myotonia congenita, Thomsen's disease, and Pompe's disease. Muscle wasting can be associated with cancer, AIDS, congestive heart failure, and chronic obstructive pulmonary disease, as well as include necrotizing myopathy of intensive care.

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein. Furthermore, genuses are recited as shorthand for a recitation of all members of the genus; for example, the recitation of (C1-C3) alkyl is shorthand for a recitation of all C1-C3 alkyls: methyl, ethyl and propyl, including isomers thereof.

The term "heteroatom" as used herein generally means any atom other than carbon or hydrogen. Preferred heteroatoms include oxygen (O), phosphorus (P), sulfur (S), nitrogen (N), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, iscyante, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2$—$CH_2$—$CH_2$—$CH_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, P, Si and S, wherein the nitrogen, sulfur, and phosphorous atoms may optionally be oxidized and the nitrogen heteroatom may optionally be quaternized. The heteroatom(s) O, N, P and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N(CH3)—$CH_3$. Up to two heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent means a divalent radical derived from heteroalkyl, as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R"', —OC(O)R', —C(O)R', —CONR'R", —OC(O)NR'R", —NR"C(O)R', —NR'-C(O)NR"R"', —NR'-SO$_2$NR"', —NR"CO$_2$R', —NH—C(NH$_2$)=NH, —NR'C(NH$_2$)=NH, —NH—C(NH$_2$)=NR', —S(O)R', —SO$_2$NR'R", —NR"SO$_2$R, —CN and —NO$_2$, in a number ranging from zero to three, with those groups having zero, one or two substituents being particularly preferred. R', R" and R"' each independently refer to hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R"', —OC(O)R', —C(O)R', —CONR'R", —OC(O)NR'R", —NR"C(O)R', —NR"CO$_2$R', —NR'—SO$_2$NR"R"', —S(O)R', —SO2R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CONR'R", —OC(O)NR'R", —NR"C(O)R', —NR"CO$_2$R', —NR'—SO$_2$NR"R"', —SO$_2$NR'R", —NR"SO$_2$R, —CN and —NO$_2$.

Similarly, substituents for the aryl and heteroaryl groups are varied and selected from: halogen, —OR', —OC(O)R', —NR'R —SR', —R', —CN, —NO$_2$, —CONR'R", —C(O)R', —OC(O)NR'R", —NR"C(O)R', —NR"CO2R', —NR'—C(O)NR"R"', —NR'—SO$_2$NR"R"', —NH—C(NH2)=NH, —NR'C(NH$_2$)=NH, —NH—C(NH$_2$)=NR', —S(O)R', —SO$_2$R, —SO$_2$NR'R", —NR"SO$_2$R, —N$_3$, —CH(Ph)$_2$, perfluoro(C1-C4)alko-xy and perfluoro(C1-C4)alkyl, in a number ranging from zero to the total number of open valences on the aromatic ring system; and where R, R" and R"' are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R, —CN, —NO$_2$, —CO$_2$R', —CONR'R", —C(O)R', —C(O)NR'R", —NR"C(O)R', —S(O)R', —SO$_2$R', —SO$_2$NR'R", —NR"SO$_2$R, —N$_3$, —CH(Ph)$_2$, perfluoro (C1-C4)alkoxy and perfluoro(C1-C4)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C1-C4)alkoxy and perfluoro(C1-C4)alkyl.

The substituent —CO$_2$H, as used herein, includes bioisosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH$_2$)q-U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula —A-(CH2)r-B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)s-X—(CH$_2$)t-, where s and t are independently integers of from 0 to 3, and X is —O—, —NR'—, —S—, —S(O)—, —S(O)$_2$—, or —S(O)$_2$NR'—. The substituent R in —NR'— and —S(O)$_2$NR'— is selected from hydrogen or unsubstituted (C1-C6)alkyl.

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, 0-3 heteroatom C1-C6 alkyl, substituted or unsubstituted, 0-3 heteroatom C2-C6 alkenyl, substituted or unsubstituted, 0-3 heteroatom C2-C6 alkynyl, or substituted or unsubstituted, 0-3 heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3).

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, diastereomers, geometric isomers and individual isomers are all intended to be encompassed within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The term "therapeutically effective amount" refers to the amount of the subject compound that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat an applicable disease or condition (herein).

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as *Remington's Pharmaceutical Science,* Mack Publishing Co, NJ (1991). In addition, the compounds may be advantageously used in conjunction with other therapeutic agents as described herein or otherwise known in the art, particularly other anti-necrosis agents. Hence the compositions may be administered separately, jointly, or combined in a single dosage unit.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The therapeutics of the invention can be administered in a therapeutically effective dosage and amount, in the process of a therapeutically effective protocol for treatment of the patient. For more potent compounds, microgram (ug) amounts per kilogram of patient may be sufficient, for example, in the range of about 1, 10 or 100 ug/kg to about 0.01, 0.1, 1, 10, or 100 mg/kg of patient weight though optimal dosages are compound specific, and generally empirically determined for each compound.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as compounds potency, severity of the disease being treated. For example, a dosage regimen of the compoundss can be oral administration of from 10 mg to 2000 mg/day, preferably 10 to 1000 mg/day, more preferably 50 to 600 mg/day, in two to four (preferably two) divided doses. Intermittent therapy (e.g., one week out of three weeks or three out of four weeks) may also be used.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES
TABLE 1
Compound List
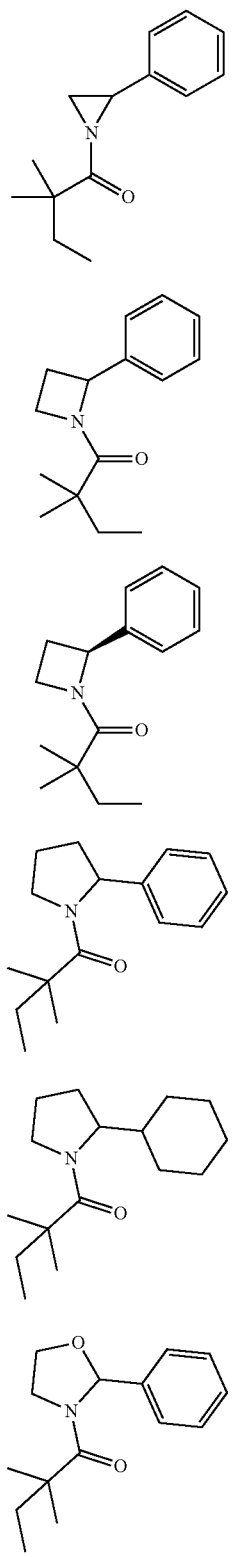
TABLE 1-continued
Compound List
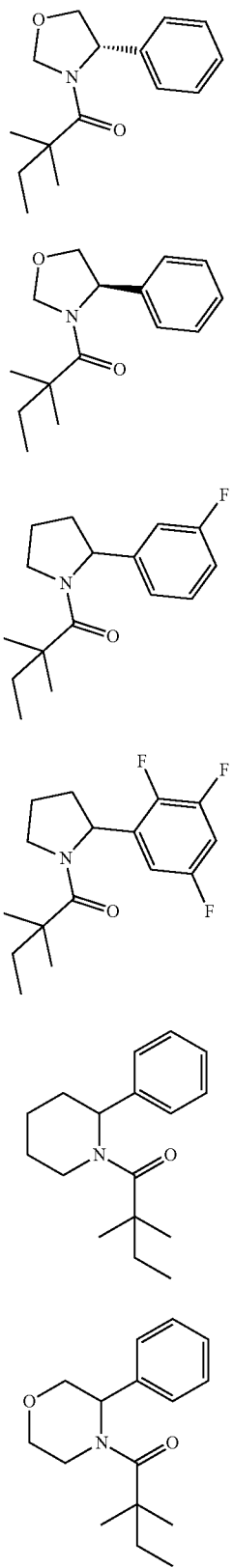

TABLE 1-continued
Compound List
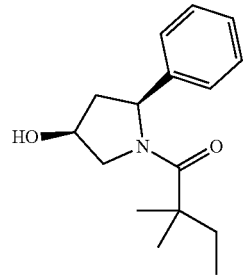 [SMILES: CCC(C)(C)C(=O)N1C[C@@H](O)C[C@H]1c1ccccc1]
13
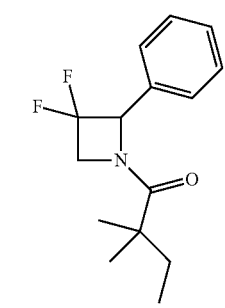 [SMILES: CCC(C)(C)C(=O)N1CC(F)(F)C1c1ccccc1]
14
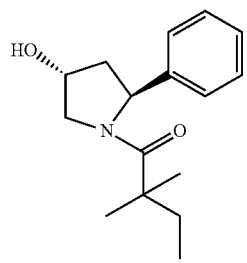 [SMILES: CCC(C)(C)C(=O)N1C[C@H](O)C[C@H]1c1ccccc1]
15
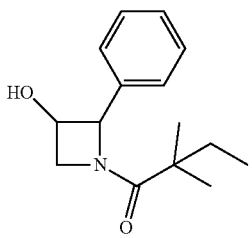 [SMILES: CCC(C)(C)C(=O)N1CC(O)C1c1ccccc1]
16
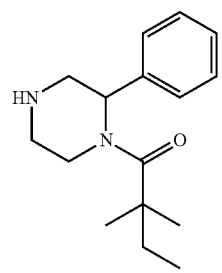
17
TABLE 1-continued
Compound List
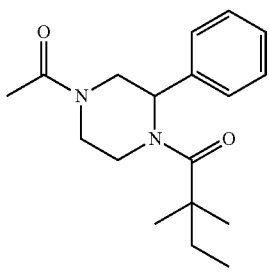 [SMILES: CCC(C)(C)C(=O)N1CCN(C(C)=O)CC1c1ccccc1]
18
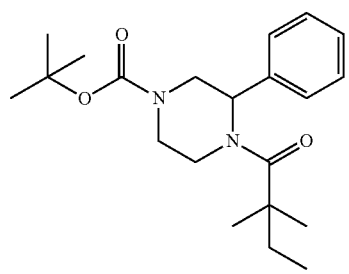 [SMILES: CCC(C)(C)C(=O)N1CCN(C(=O)OC(C)(C)C)CC1c1ccccc1]
19
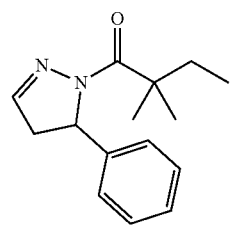 [SMILES: CCC(C)(C)C(=O)N1N=CCC1c1ccccc1]
20
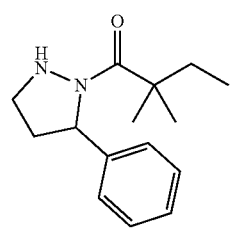 [SMILES: CCC(C)(C)C(=O)N1NCCC1c1ccccc1]
21
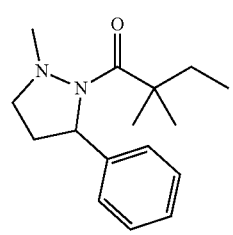 [SMILES: CCC(C)(C)C(=O)N1C(c2ccccc2)CCN1C]
22
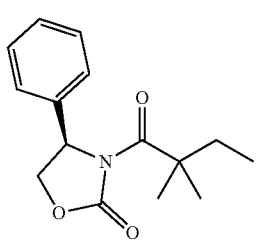 [SMILES: CCC(C)(C)C(=O)N1C(=O)OC[C@H]1c1ccccc1]
23

TABLE 1-continued
Compound List
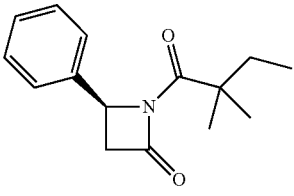 [SMILES: CCC(C)(C)C(=O)N1C(=O)C[C@H]1c1ccccc1] 24
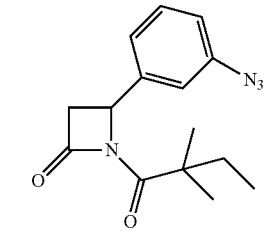 [SMILES: CCC(C)(C)C(=O)N1C(=O)CC1c1cccc(N=[N+]=[N-])c1] 25
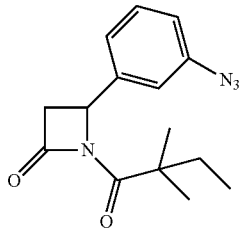 26
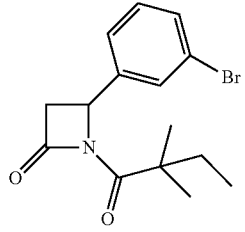 27
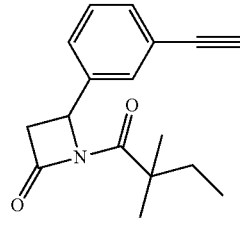 [SMILES: C#Cc1cccc(C2CC(=O)N2C(=O)C(C)(C)CC)c1] 28
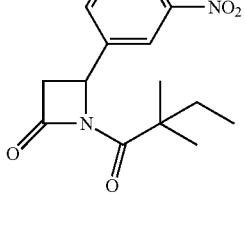 29
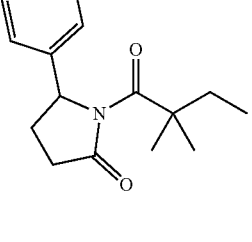 30
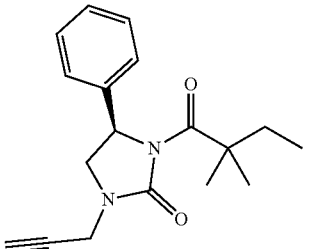 31
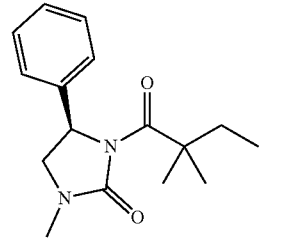 [SMILES: CCC(C)(C)C(=O)N1C(=O)N(C)C[C@H]1c1ccccc1] 32
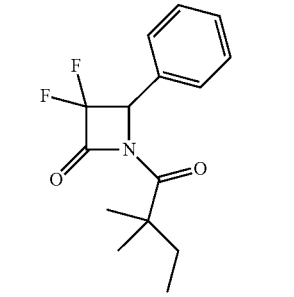 [SMILES: CCC(C)(C)C(=O)N1C(=O)C(F)(F)C1c1ccccc1] 33
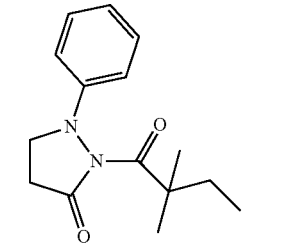 [SMILES: CCC(C)(C)C(=O)N1C(=O)CCN1c1ccccc1] 34
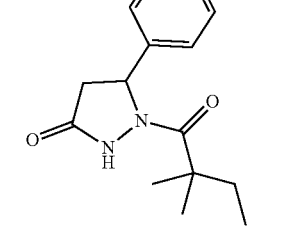 35

TABLE 1-continued
Compound List
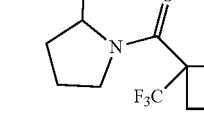 36
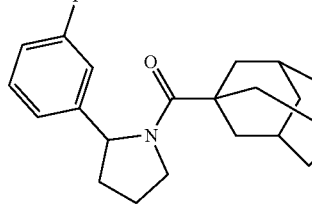 37
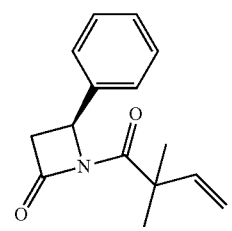 [SMILES: C=CC(C)(C)C(=O)N1C(=O)C[C@H]1c1ccccc1] 38
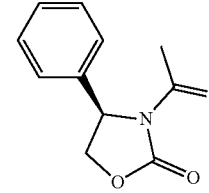 39
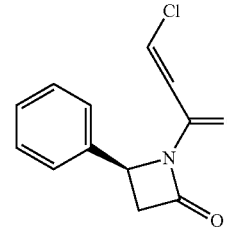 40
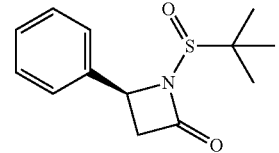 [SMILES: CC(C)(C)S(=O)N1C(=O)C[C@H]1c1ccccc1] 41
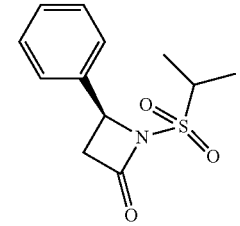 [SMILES: CC(C)S(=O)(=O)N1C(=O)C[C@H]1c1ccccc1] 42
TABLE 1-continued
Compound List
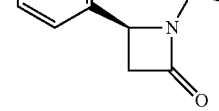 43
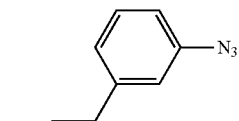 44
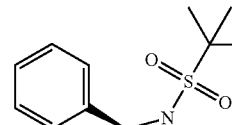 45
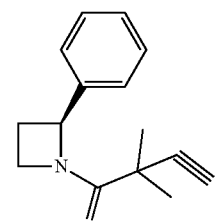 46
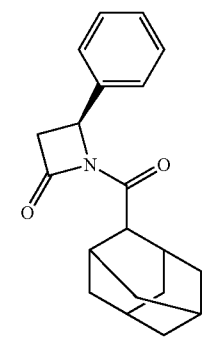 [SMILES: O=C1C[C@@H](c2ccccc2)N1C(=O)C1C2CC3CC(C2)CC1C3] 47
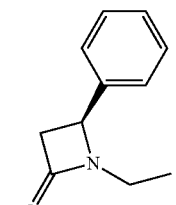 48

TABLE 1-continued
Compound List
| | |
|---|---|
| 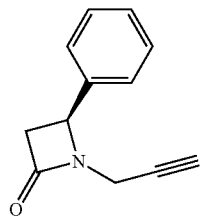 | 49 |
| 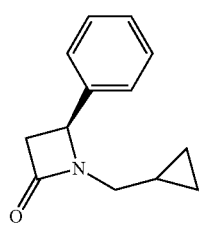 [SMILES: O=C1C[C@@H](c2ccccc2)N1CC1CC1] | 50 |
| 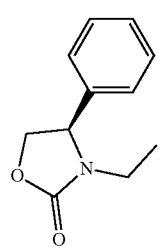 | 51 |
| 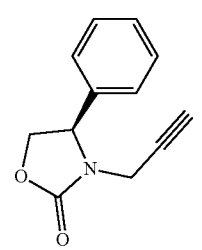 | 52 |
| 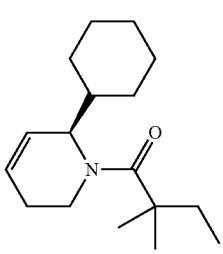 [SMILES: CCC(C)(C)C(=O)N1CCC=C[C@H]1C1CCCCC1] | 53 |
| 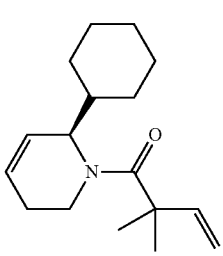 [SMILES: C=CC(C)(C)C(=O)N1CCC=C[C@H]1C1CCCCC1] | 54 |
| 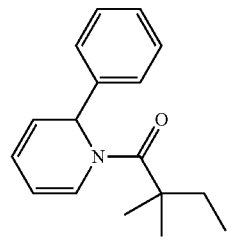 [SMILES: CCC(C)(C)C(=O)N1C=CC=CC1c1ccccc1] | 55 |
| 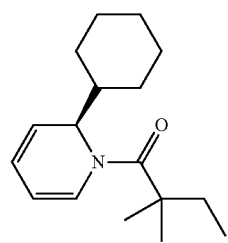 [SMILES: CCC(C)(C)C(=O)N1C=CC=C[C@H]1C1CCCCC1] | 56 |
| 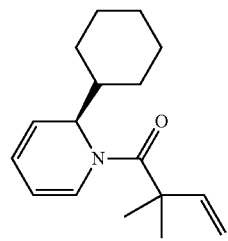 [SMILES: C=CC(C)(C)C(=O)N1C=CC=C[C@H]1C1CCCCC1] | 57 |
| 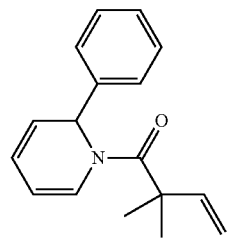 [SMILES: C=CC(C)(C)C(=O)N1C=CC=CC1c1ccccc1] | 58 |
| 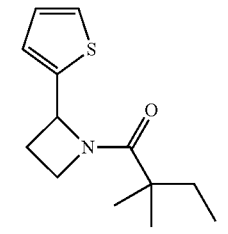 [SMILES: CCC(C)(C)C(=O)N1CCC1c1cccs1] | 59 |
| 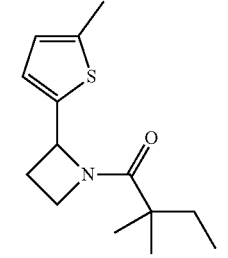 [SMILES: CCC(C)(C)C(=O)N1CCC1c1ccc(C)s1] | 60 |

TABLE 1-continued
Compound List
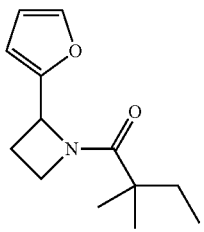 [SMILES: CCC(C)(C)C(=O)N1CCC1c1ccco1] 61
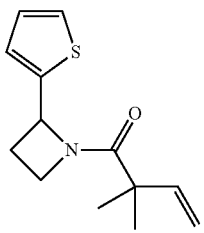 [SMILES: C=CC(C)(C)C(=O)N1CCC1c1cccs1] 62
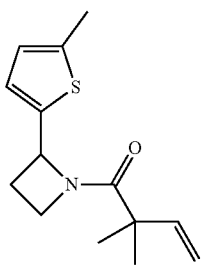 [SMILES: C=CC(C)(C)C(=O)N1CCC1c1ccc(C)s1] 63
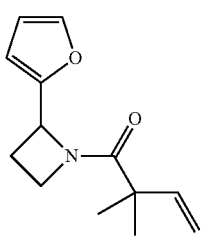 [SMILES: C=CC(C)(C)C(=O)N1CCC1c1ccco1] 64
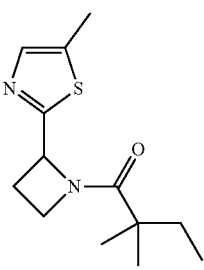 [SMILES: CCC(C)(C)C(=O)N1CCC1c1ncc(C)s1] 65
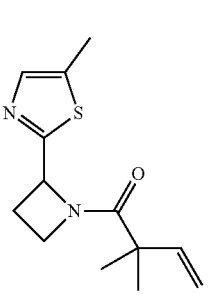 [SMILES: C=CC(C)(C)C(=O)N1CCC1c1ncc(C)s1] 66
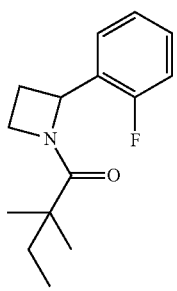 [SMILES: CCC(C)(C)C(=O)N1CCC1c1ccccc1F] 67
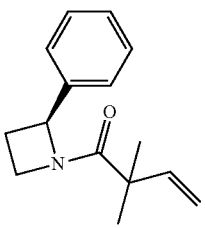 [SMILES: C=CC(C)(C)C(=O)N1CC[C@H]1c1ccccc1] 68
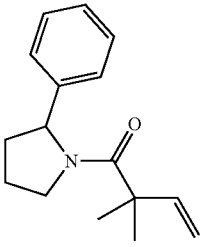 [SMILES: C=CC(C)(C)C(=O)N1CCCC1c1ccccc1] 69
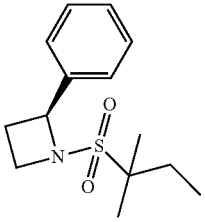 [SMILES: CCC(C)(C)S(=O)(=O)N1CC[C@H]1c1ccccc1] 70
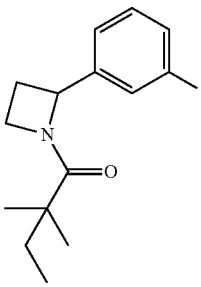 71
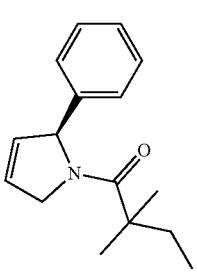 [SMILES: CCC(C)(C)C(=O)N1CC=C[C@H]1c1ccccc1] 72

TABLE 1-continued
Compound List
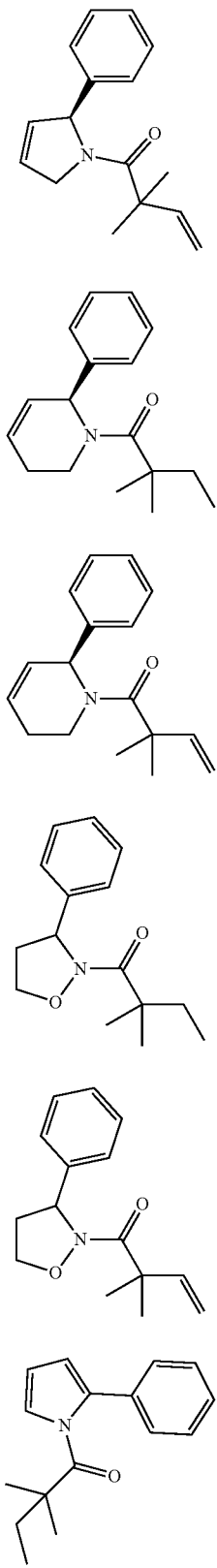
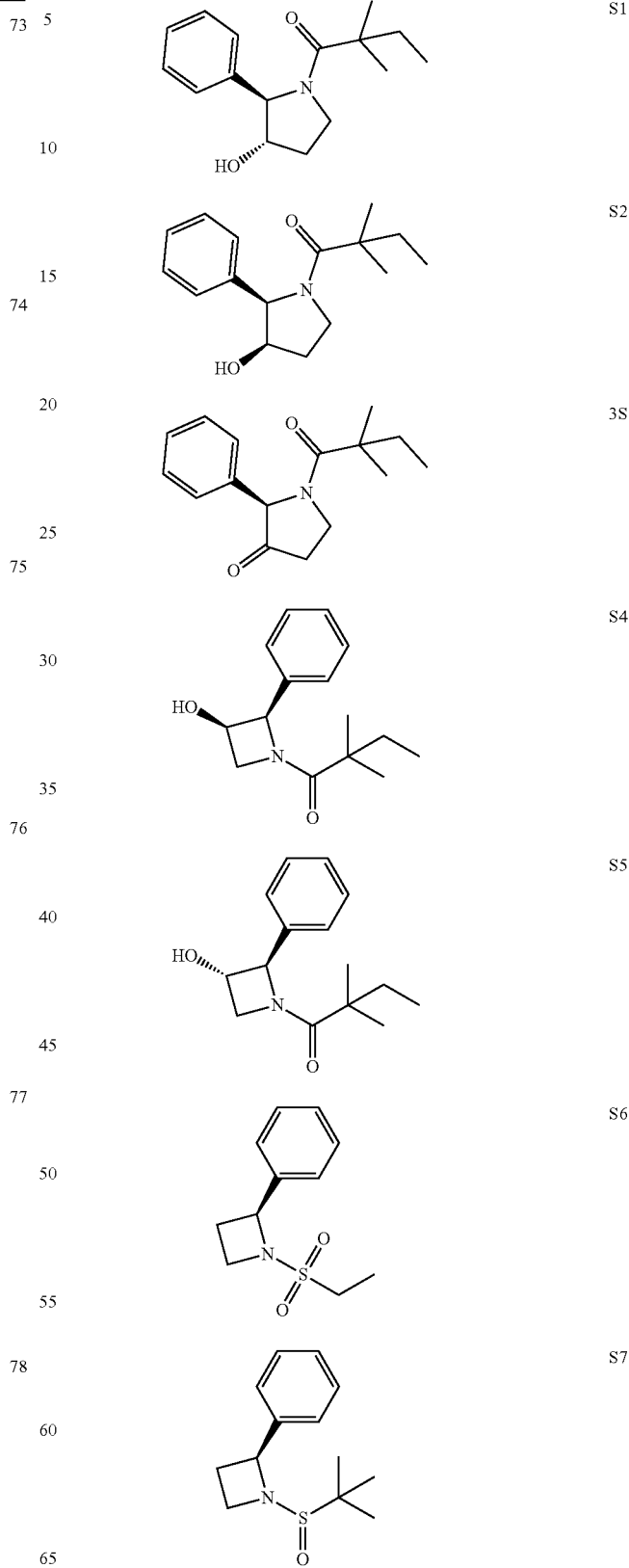

TABLE 1-continued

Compound List

2. Compound Preparation

Compound 1: Preparation of 2,2-dimethyl-1-(2-phenylaziridin-1-yl)butan-1-one

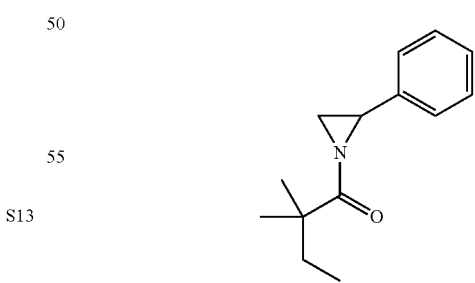

2-phenylaziridine (35 mg, 0.294 mmoL) and triethylamine (59.4 mg, 0.588 mmol) were dissolved in 1.5 mL of dry $CH_2Cl_2$. 2,2-dimethylbutanoyl chloride (43.3 mg, 0.323 mmol) in 1 mL of $CH_2Cl_2$ was added slowly to the solution at 0° C. under nitrogen. The mixture was stirred at room temperature for 2 h, diluted with $CH_2Cl_2$ and water. The organic layer were washed with saturated NaHCO₃, brine, dried with Na₂SO₄ and concentrated .The residue was purified by chromatography to give compound 1 (20 mg, 31%) as a colorless oil ¹HNMR (CDCl₃, 400 MHz): δ7.36-7.44 (m, 5 H), 5.90 (dd, 1 H, J=9.2, 4.0 Hz), 3.44 (dd, 1 H, J=13.6, 9.2 Hz), 3.26 (dd, 1 H, J=4.0, 13.6 Hz), 1.61 (qd, 2 H, J=7.6, 2.4 Hz), 1.21 (s, 3 H), 1.19 (s, 3 H), 0.74 (t, 3 H, J=7.6 Hz). LC-MS (ESI) [M+H]⁺ calad for C₁₄H₁₉NO, 218.1; found, 218.3.

Compound 2: Preparation of 2,2-dimethyl-1-(2-phenylazetidin-1-yl)butan-1-one

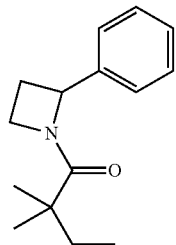 [SMILES: CCC(C)(C)C(=O)N1CCC1c1ccccc1]

The titled compound 2 was prepared in 77% yield from 2-phenylazetidine (50 mg) and 2,2-dimethylbutanoyl chloride (55 mg) according to the procedure outlined for compound 1. ¹HNMR (CDCl₃, 400 MHz): δ 7.31-7.36 (m, 4 H), 7.23-7.28 (m, 1 H), 5.35-5.39 (m, 1 H), 4.34-4.46 (m, 2 H), 2.66-2.74 (m, 1 H), 2.07-2.14 (m, 1 H), 1.59 (q, 2 H, J=7.6 Hz), 1.14 (s, 6 H), 0.89 (t, 3 H, J=7.6 Hz). LC-MS (ESI) [M+H]⁺ calad for C₁₅H₂₁NO, 232.2; found, 232.4

Compound 3: Preparation of (S)-2,2-dimethyl-1-(2-phenylazetidin-1-yl)butan-1-one

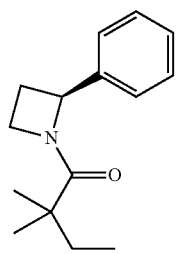 [SMILES: CCC(C)(C)C(=O)N1CC[C@H]1c1ccccc1]

The titled compound 3 was prepared in 77% yield from (S)-2-phenylazetidine (50 mg) and 2,2-dimethylbutanoyl chloride (55 mg) according to the procedure outlined for compound 1. ¹HNMR (CDCl₃, 400 MHz): δ7.32-7.37 (m, 4 H), 7.22-7.24 (m, 1 H), 5.37 (dd, 1 H, J=8.8, 6.4 Hz), 4.26-4.45 (m, 2 H), 2.66-2.75 (m, 1 H), 2.07-2.15 (m, 1 H), 1.58 (q, 2 H, J=7.6 Hz), 1.15 (s, 6 H), 0.87 (t, 3 H, J=7.6 Hz). LC-MS (ESI) [M+H]⁺ calad for C₁₅H₂₁NO, 232.2; found, 232.4.

Compound 4: Preparation of 2,2-dimethyl-1-(2-phenylpyrrolidin-1-yl)butan-1-one

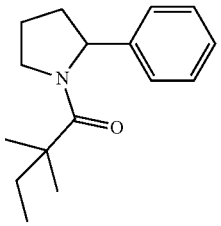 [SMILES: CCC(C)(C)C(=O)N1CCCC1c1ccccc1]

The titled compound 4 was prepared in 46% yield from 2-phenylpyrrolidine (50 mg) and 2,2-dimethylbutanoyl chloride (55 mg) according to the procedure outlined for compound 1. ¹HNMR (CDCl₃, 400 MHz): δ7.28-7.30 (m, 1 H), 7.15-7.20 (m, 3 H), 5.25 (m, 1 H), 3.82 (t, 2 H, J=6.4 Hz), 2.17-2.26 (m, 1 H), 1.78-2.01 (m, 3 H), 1.59-1.67 (m, 2 H), 1.23 (s, 6 H), 0.85 (t, 3 H, J=7.2 Hz). LC-MS (ESI) [M+H]⁺ calad for C₁₆H₂₃NO, 246.2; found 246.4.

Compound 5: Preparation of 1-(2-cyclohexylpyrrolidin-1-yl)-2,2-dimethylbutan-1-one

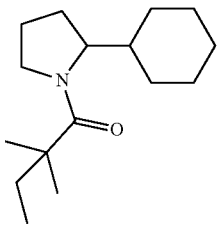 [SMILES: CCC(C)(C)C(=O)N1CCCC1C1CCCCC1]

The titled compound 5 was prepared in 46% yield from 2-cyclohexylpyrrolidine (70 mg) and 2,2-dimethylbutanoyl chloride (73 mg) according to the procedure outlined for compound 1. ¹HNMR (CDCl₃, 400 MHz): δ4.13-4.18 (m, 1 H), 3.74-3.80 (m, 1 H), 3.27-3.33 (m, 1 H), 1.87-2.00 (m, 5 H), 1.65-1.82 (m, 6 H), 1.53-1.60 (m, 2 H), 1.22 (s, 6 H), 0.92-1.18 (m, 4 H), 0.87 (t, 3 H, J=7.6 Hz). LC-MS (ESI) [M+H]⁺ calad for C₁₆H₂₉NO, 252.2; found 252.4.

Compound 6: Preparation of 2,2-dimethyl-1-(2-phenyloxazolidin-3-yl)butan-1-one

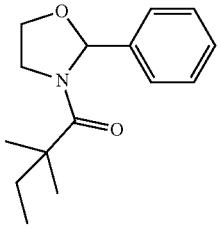

The titled compound 6 was prepared in 46% yield from 2-phenyloxazolidine (80 mg) and 2,2-dimethylbutanoyl chloride (108 mg) according to the procedure outlined for compound 1. ¹HNMR (CDCl₃, 400 MHz):δ7.87-7.90 (m, 2

H), 7.61-7.66 (m, 1 H), 7.52-7.56 (m, 2 H), 6.14 (brs, 1 H), 3.72 (t, 2 H, J=4.8 Hz), 3.43 (dd, 2 H, J=10.0, 5.6 Hz), 1.55 (q, 2 H, J=7.6 Hz), 1.16 (s, 6 H), 0.85 (t, 3 H, J=7.6 Hz). LC-MS (ESI) [M+H]+ calad for $C_{15}H_{21}NO_2$, 248.2; found, 248.4.

Compound 7: Preparation of (S)-2,2-dimethyl-1-(4-phenyloxazolidin-3-yl)butan-1-one

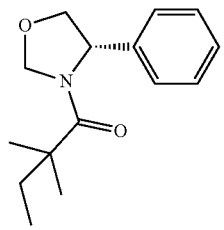 [SMILES: CCC(C)(C)C(=O)N1COC[C@@H]1c1ccccc1]

The titled compound 7 was prepared in 46% yield from (S)-4-phenyloxazolidine (57 mg) and 2,2-dimethylbutanoyl chloride (102 mg) according to the procedure outlined for compound 1. $^1$HNMR (CDCl$_3$, 400 MHz): δ7.30-7.34 (m, 2 H), 7.23-7.26 (m, 3 H), 5.29 (dd, 2 H, J=10.4, 4.4 Hz), 5.21 (dd, 1 H, J=6.4, 4.4 Hz), 4.23 (dd, 1 H, J=8.8, 6.4 Hz), 3.88 (dd, 1 H, J=8.8, 4.4 Hz), 1.53-1.59 (m, 2 H), 1.17 (s, 3 Hz), 1.16 (s, 3 H), 0.81 (t, 3 H, J=7.6 Hz). LC-MS (ESI) [M+H]+ calad for $C_{15}H_{21}NO_2$, 248.2; found, 248.4.

Compound 8: Preparation of (R)-2,2-dimethyl-1-(4-phenyloxazolidin-3-yl)butan-1-one

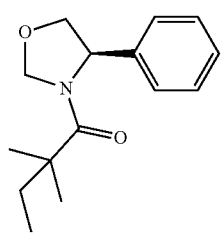 [SMILES: CCC(C)(C)C(=O)N1COC[C@H]1c1ccccc1]

The titled compound 8 was prepared in 46% yield from (R)-4-phenyloxazolidine (80 mg) and 2,2-dimethylbutanoyl chloride (86 mg) according to the procedure outlined for compound 1. $^1$HNMR (CDCl$_3$, 400 MHz): 7.40-7.42 (m, 2 H), 7.30-7.33 (m, 3 H), 5.29 (dd, 2 H, J=4.4, 10.4 Hz), 5.21 (dd, 1 H, J=4.0, 6.4 Hz), 4.23 (dd, 1 H, J=8.4, 6.4 Hz), 3.87 (dd, 1 H J=4.0, 8.4 Hz), 1.53-1.60 (m, 2 H), 1.15 (s, 3 H), 1.17 (s, 3 H), 0.811 (t, 3 H, J=7.2 Hz). LC-MS (ESI) [M+H]+ calad for $C_{15}H_{21}NO_2$, 248.2; found 248.4.

Compound 9: Preparation of 1-(2-(3-fluorophenyl)pyrrolidin-1-yl)-2,2-dimethylbutan-1-one

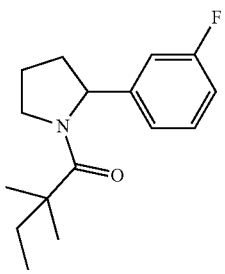 [SMILES: CCC(C)(C)C(=O)N1CCCC1c1cccc(F)c1]

The titled compound 9 was prepared in 66% yield from 2-(3-fluorophenyl)pyrrolidine (95 mg) and 2,2-dimethylbutanoyl chloride (93 mg) according to the procedure outlined for compound 1. $^1$HNMR (CDCl$_3$, 400 MHz): δ 7.21-7.25 (m, 1 H), 6.80-6.94 (m, 3 H), 5.22 (m, 1 H), 3.82 (t, 2 H, J=6.8 Hz), 2.17-2.26 (m, 1 H), 1.87-2.01(m, 2 H), 1.70-1.78 (m, 1 H), 1.59-1.69 (m, 2 H), 1.24 (s, 3 H), 1.21 (s, 3 H), 0.86 (t, 3 H, J=7.2 Hz). LC-MS (ESI) [M+H]+ calad for $C_{16}H_{22}FNO$, 264.2; found, 264.4.

Compound 10: Preparation of 2,2-dimethyl-1-(2-(2,3,5-trifluorophenyl)pyrrolidin1-yl)butan-1-one

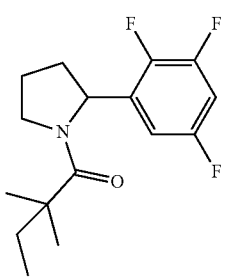 [SMILES: CCC(C)(C)C(=O)N1CCCC1c1cc(F)cc(F)c1F]

The titled compound 10 was prepared in 66% yield from 2-(2,3,5-trifluorophenyl)pyrrolidine (50 mg) and 2,2-dimethylbutanoyl chloride (34 mg) according to the procedure outlined for compound 1. $^1$HNMR (CDCl$_3$, 400 MHz): δ 6.66-6.71 (m, 1 H), 6.44-6.46 (m, 1 H), 5.43-5.46 (m, 1 H), 3.79-3.86 (m, 2 H), 2.21-2.26 (m, 1 H), 1.90-1.98 (m, 2 H), 1.69-1.77 (m, 1 H), 1.61-1.68 (m, 2 H), 1.26 (s, 3 H), 1.23 (s, 3 H), 0.89 (t, 3 H, J=7.6 Hz). LC-MS (ESI) [M+H]+ calad for $C_{16}H_{20}F_3NO$, 300.1; found, 300.4.

Compound 11: Preparation of 2,2-dimethyl-1-(2-phenylpiperidin-1-yl)butan-1-one

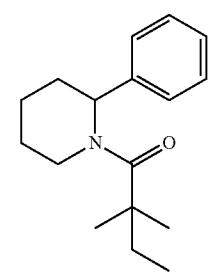 [SMILES: CCC(C)(C)C(=O)N1CCCCC1c1ccccc1]

The titled compound 11 was prepared in 53% yield from 2-phenylpiperidine (50 mg) and 2,2-dimethylbutanoyl chloride (50 mg) according to the procedure outlined for compound 1. ¹HNMR (CDCl₃, 400 MHz): δ7.32-7.36 (m, 2 H), 7.22-7.24 (m, 3 H), 5.98 (m, 1 H), 4.09 (m, 1 H), 2.90 (m, 1 H), 2.42 (d, 1 H, J=14 Hz), 1.83-1.91 (m, 1 H), 1.65-1.71 (m, 4 H), 1.51-1.61 (m, 2 H), 1.32 (s, 3 H), 1.29 (s, 3 H), 0.98 (t, 3 H, J=7.6 Hz). LC-MS (ESI) [M+H]⁺ calad for C₁₇H₂₅NO, 260.2; found 260.4.

Compound 12: Preparation of
2,2-dimethyl-1-(3-phenylmorpholino)butan-1-one

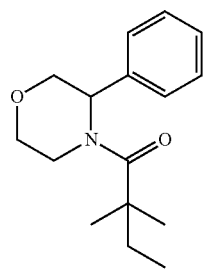 [SMILES: CCC(C)(C)C(=O)N1CCOCC1c1ccccc1]

The titled compound 12 was prepared 20% yield from 3-phenylmorpholine (25 mg) and 2,2-dimethylbutanoyl chloride (23 mg) according to the procedure outlined for compound 1. ¹HNMR (CDCl₃, 400 MHz): δ 7.47-7.52 (m, 2 H), 7.32-7.36 (m, 2 H), 7.25-7.28 (m, 1 H), 5.54-5.76 (m, 1 H), 4.50 (d, 1 H, J=12.0 Hz), 3.83-3.91 (m, 3 H), 3.56-3.62 (td, 1 H, J=2.4, 12.0 Hz), 3.27-3.31 (m, 1 H), 1.59 (q, 2 H, J=7.6 Hz), 1.26 (s, 6 H), 0.90 (t, 3 H, J=7.6 Hz). LC-MS (ESI) [M+H]⁺ calad for C₁₆H₂₃NO₂, 262.2; found, 262.4.

Compound 13: Preparation of 1-((2S,4S)-4-hydroxy-2-phenylpyrrolidin-1-yl)-2,2-dimethylbutan-1-one

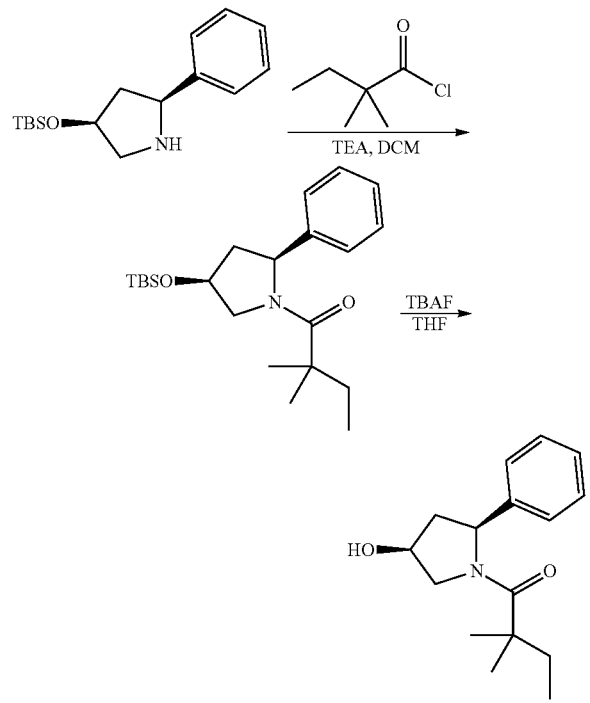

(2S,4S)-4-((tert-butyldimethylsilyl)oxy)-2-phenylpyrrolidine (185 mg) and trimethylamine (0.18 ml) were dissolved in in 2 mL of dry dichloromethane. The mixture was cooled to 0° C. and 2,2-dimethylbutanoyl chloride (134 mg) was added, then allowed to warm to room temperature and stirred for 16 h. The mixture was diluted with dichloromethane and water. The aqueous layer was extracted with dichloromethane. The organic layers were combined and concentrated. The residue was purified by column chromatography to give 1-((2S,4S)-4-((tert-butyldimethylsilyl)oxy)-2-phenylpyrrolidin-1-yl)-2,2-dimethylbutan-1-one (130 mg, 52%). ¹H-NMR (CDlC3): 7.11-7.29 (M, 5H), 5.10-5.20 (m, 1H), 4.31-4.37 (m, 1H), 4.12 (dd, J=6.0, 10.4 Hz), 3.62 (dd, J=6.4, 10.4 Hz), 2.46-2.52 (m, 1H), 1.80-1.84 (m, 1H), 1.57-1.72 (m, 2 H), 1.24 (s, 3 H), 1.22 (s, 3 H), 0.84-0.87 (m, 12 H), 0.09 (s, 3 H), 0.01 (s, 3 H).

The above intermediate (50 mg) was dissolved in THF (4 ml) and TBAF (42 mg) was added. The mixture was stirred at room temperature for 16 h, diluted with dichloromethane and water. The aqueous layer was extracted with dichloromethane. The organic layers were combined and concentrated. The residue was purified by column chromatography to give compound 13 (20 mg, 57%) as a white solid. ¹H-NMR (CDCl3): δ7.28-7.32 (m, 2 H), 7.17-7.24 (m, 3 H), 5.24-5.32 (m, 1 H), 4.45-4.51 (m, 1 H), 4.15 (dd, 1 H, J=5.6, 11.2 Hz), 3.76 (dd, 1 H, J=4.4, 11.2 Hz), 2.50-2.57 (m, 1 H), 1.90-1.95 (m, 1 H), 1.60-1.69 (m, 2 H), 1.25 (s, 3 H), 1.21 (s, 3 H), 0.86 (t, 3 H, J=7.6 Hz). MS(ES) [M+H]⁺ calad for C₁₆H₂₃NO₂, 262.2; found, 262.2.

Compound 14: Preparation of 1-(3,3-difluoro-2-phenylazetidin-1-yl)-2,2-dimethylbutan-1-one

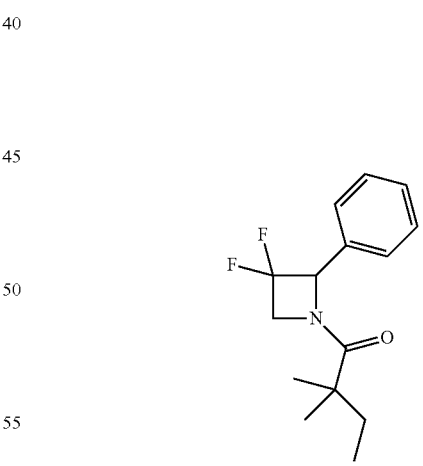

The titled compound 14 was prepared in 46% yield from 3,3-difluoro-2-phenylazetidine (25 mg) and 2,2-dimethylbutanoyl chloride (40 mg) according to the procedure outlined for compound 1. ¹H NMR (CDCl₃, 400 MHz): δ7.34-7.42 (m, 3 H), 7.27-7.29 (m, 2 H), 5.60-5.66 (m, 1 H), 4.54-4.69 (m, 2 H), 1.60 (q, 2 H, J=7.6 Hz), 1.17 (s, 3 Hz), 1.15 (s, 3 Hz), 0.89 (t, 3 H, J=7.6 Hz). LC-MS (ESI) [M+H]⁺ calad for C₁₅H₁₉F₂NO, 268.1; found, 268.1.

Compound 15: Preparation of 1-((2S,4R)-4-hydroxy-2-phenylpyrrolidin-1-yl)-2,2-dimethylbutan-1-one

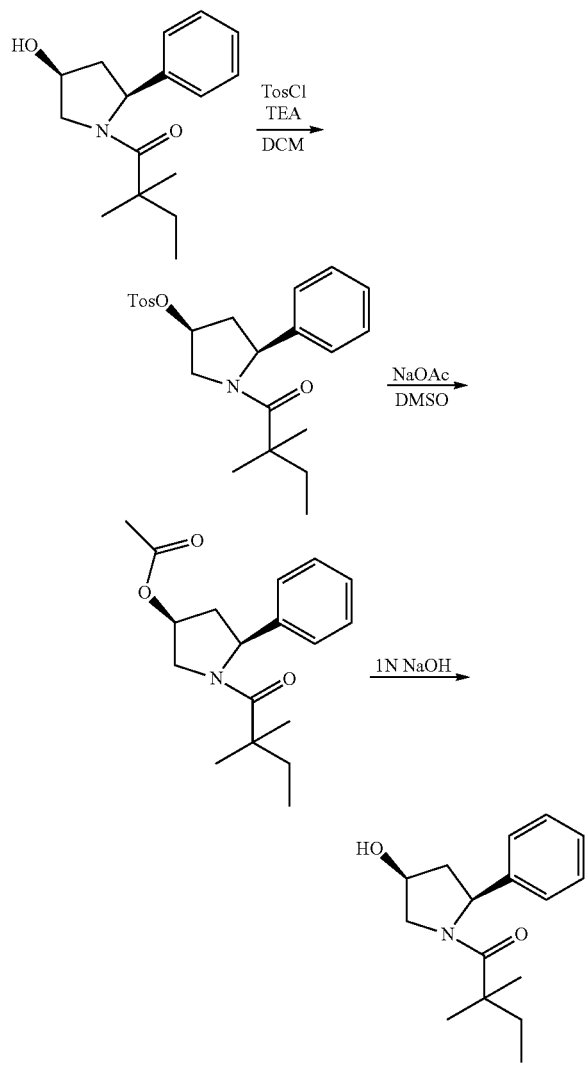

To a solution of compound (30 mg) in dry DCM (4 Ml) was added 4-toluene sulfonyl chloride (27 mg) and the mixture was stirred at room temperature for 16 h and quenched with water (2 ml). The aqueous layers were extracted with DCM (15 mL×3) and the organic layers was combined, washed with brine, dried with $Na_2SO_4$ and evaporated to dryness. The residue was purified by column chromatography to give (3S,5S)-1-(2,2-dimethylbutanoyl)-5-phenylpyrrolidin-3-yl 4-methylbenzenesulfonate (38.1 mg, 80%) as a white solid. $^1H$ NMR: ($CDCl_3$, 400 MHz): δ7.55(d, 2 H, J=8.0 Hz), 7.20-7.26 (m, 3H), 7.08-7.18 (m, 3 H), 5.18-5.21(m, 1 H), 5.06-5.11 (m, 1 H), 4.13-4.18 (m, 1 H), 3.90-3.94 (m, 1 H), 2.42 (s, 3 H), 2.40-2.47 (m, 1 H), 1.95-1.99 (m, 1 H) 1.51-1.60 (m, 2 H), 1.14 (s, 3 H), 1.16 (s, 3 H), 0.79(t, 3 H, J=7.6 Hz). The above intermediate was dissolved in dry DMSO (2 ml) and sodium acetate trihydrate (12 mg) was added. The mixture was stirred at 120° C. for 60 h and 4 ml of water was added. The aqueous layers were extracted with DCM (15 mL×3) and the organic layers was combined, washed with brine, dried with $Na_2SO_4$ and evaporated to dryness. The residue was purified by column chromatography to give (3R, 5S)-1-(2,2-dimethylbutanoyl)-5-phenylpyrrolidin-3-ylacetate (13 mg, 47%). $^1H$ NMR: ($CDCl_3$, 400 MHz): δ7.27-7.31 (m, 2H), 7.16-7.22 (m, 3 H), 5.27-5.32 (m, 2 H), 5.12 (d, 2 H, J=12.0 Hz), 3.91 (dd, 1 H, J=4.0, 12.0 Hz), 2.42-2.49 (m, 1 H), 2.06 (s, 3 H), 1.52-1.61 (m, 2 H), 1.22 (s, 3 H), 1.19 (s, 3 H), 0.84 (t, 3 H, J=7.6 Hz).

The above intermediate (13 mg) was dissolved in THF (1 ml) and MeOH (0.2 ml) and 0.01 mL 1N NaOH was added. The mixture was stirred at 0° C. for 1 h andneutralized with 1N HCl. The aqueous layers were extracted with DCM and the organic layers was combined and evaporated to dryness. The residue was purified by Pre-HPLC to give the titled compound 15 (4 mg, 36%). $^1H$ NMR: ($CDCl_3$, 400 MHz): δ7.27-7.36 (m, 2 H), 7.13-7.21 (m, 3 H), 5.32 (t, 1 H, J=7.6 Hz), 4.53-4.57 (m, 1 H), 3.88-3.96 (m, 2 H), 2.27-2.34 (m, 1 H), 1.94-2.02 (m, 1 H), 1.64-1.75 (m, 2 H), 1.23 (s, 3 H), 1.21 (s, 3 H), 0.86 (t, 3 H, J=7.6 Hz). LC-MS (ESI) $[M+H]^+$ calad for $C_{16}H_{23}NO_2$, 262.2; found, 262.2

Compound 16: Preparation of 1-(3-hydroxy-2-phenylazetidin-1-yl)-2,2-dimethylbutan-1-one

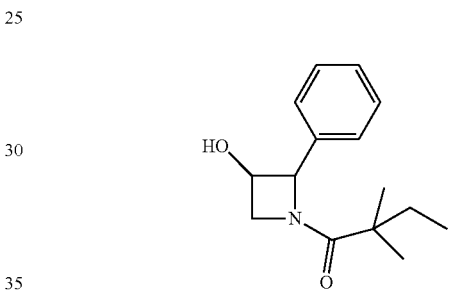

To a solution of 2-phenylazetidin-3-ol (27 mg) in THF (2 ml) and $H_2O$ (2 ml) was added sat. $NaHCO_3$ (0.5 ml). The mixture was stirred at room temperature for 30 min, and cooled to 0° C., 2,2-dimethylbutanoyl chloride (37 mg) was added to the mixture and stirred for overnight. The mixture was extracted with DCM and the combined organic layers were washed with water and concentrated. The crude product was purified by Pre-HPLC to give compound 16 (5 mg, 12%) as a white solid. 1H NMR: (CDCl3, 400 M z): δ7.29-7.44(m, 5 H), 5.62-5.64 (m, 1 H), 4.73-4.78 (m, 1 H), 4.63-4.69 (m, 1 H), 4.11-4.24 (m, 1 H), 1.60 (q, 2 H, J=7.6 Hz), 1.20 (s, 6 H), 0.89 (t, 3 H, J=7.6 Hz). LC-MS (ESI) [M+H]+ calad for C15H21NO2, 248.2, found, 248.4

Compound 17: Preparation of 2,2-dimethyl-1-(2-phenylpiperazin-1-yl)butan-1-one

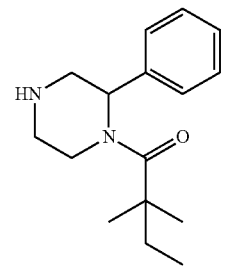 [SMILES: CCC(C)(C)C(=O)N1CCNCC1c1ccccc1]

tert-butyl 4-(2,2-dimethylbutanoyl)-3-phenylpiperazine-1-carboxylate (0.8 g) was dissolved in 3 ml of EtOAc, then 4N HCl in EtOAc (10 ml) was added. The mixture was stirred at room temperature for 3 h. After removing solvent, the residue was washed with petroleum ether to get compound 150 (0.45 g, 68%) as HCl salt, which was used for next step without further purification. $^1$HNMR (CD3OD, 400 MHz): δ7.43-7.47 (m, 2 H), 7.29-7.36 (m, 3 H), 5.93-5.99 (m, 1 H), 4.54 (d, 1 H, J=14.8 Hz), 4.14 (d, 1 H, J=13.6 Hz), 3.41-3.48 (m, 2 H), 3.26-3.29 (m, 1 H), 3.13-3.21 (m, 1 H), 1.69-1.79 (m, 2 H), 1.32 (s, 3 H), 1.29 (s, 3 H), 0.96 (t, 3 H, J=7.2 Hz). LC-MS (ESI) [M+H]$^+$ calad for $C_{16}H_{24}N_2O$, 261.2; found, 261.4.

Compound 18: Preparation of 1-(4-acetyl-2-phenylpiperazin-1-yl)-2,2-dimethylbutan-1-one

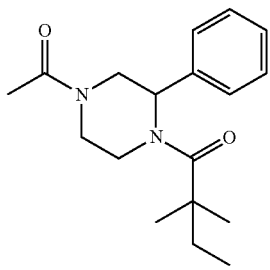 [SMILES: CCC(C)(C)C(=O)N1CCN(C(C)=O)CC1c1ccccc1]

The titled compound 18 was prepared in 52% yield from compound 17 (20 mg) and acetyl chloride (6.4 mg) according to the procedure outlined for compound 1. $^1$HNMR (CDCl$_3$, 400 MHz): δ1H-NMR (CDCl3) δ 7.27-7.35 (m, 5 H), 5.75-5.77(m, 1 H), 4.27-4.30 (m, 1 H), 4.11-4.21 (m, 2 H), 3.58-3.64 (m, 2 H), 3.23-3.30 (m, 1 H), 2.03 (s, 3 H), 1.61-1.66 (m, 2 H), 1.29 (s, 3 H), 1.28 (s, 3 H), 0.95 (t, 3 H, J=8.0 Hz). LC-MS (ESI) [M+H]$^+$ calad for $C_{18}H_{26}N_2O_2$, 303.2; found, 303.4.

Compound 19: Preparation of tert-butyl 4-(2,2-dimethylbutanoyl)-3-phenylpiperazine-1-carboxylate

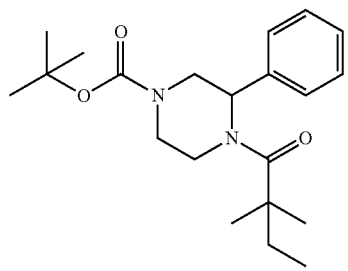 [SMILES: CCC(C)(C)C(=O)N1CCN(C(=O)OC(C)(C)C)CC1c1ccccc1]

The titled compound 19 was prepared in 90% yield from tert-butyl3-phenylpiperazine-1-carboxylate (500 mg) and 2,2-dimethylbutanoyl chloride (282 mg) according to the procedure outlined for compound 1. $^1$HNMR (CDCl$_3$, 400 MHz): δ7.31-7.34 (m, 4 H), 7.22-7.25 (m, 1 H), 5.76-5.86 (m, 1 H), 4.55-4.70 (m, 1 H), 3.75-4.15 (m, 2 H), 2.80-3.30 (m, 3 H), 1.68 (q, 2 H, J=7.6 Hz), 1.47 (s, 9 H), 1.30 (s, 3 H), 1.29 (s, 3 H), 0.95 (t, 3 H, J=7.6 Hz). LC-MS (ESI) [M+H]$^+$ calad for $C_{21}H_{32}N_2O_3$, 361.2; found 361.4.

Compound 20: Preparation of 2,2-dimethyl-1-(5-phenyl-4,5-dihydro-1H-pyrazol-1-yl)butan-1-one

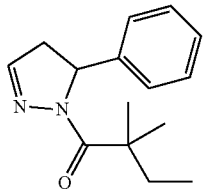 [SMILES: CCC(C)(C)C(=O)N1N=CCC1c1ccccc1]

The titled compound 20 was prepared in 46% yield from 5-phenyl-4,5-dihydro-1H-pyrazole (60 mg) and 2,2-dimethylbutanoyl chloride (56 mg) according to the procedure outlined for compound 1. $^1$HNMR (CDCl$_3$, 400 MHz): δ7.27-7.32 (m, 2 H), 7.20-7.24 (m, 1 H), 7.14-7.17 (m, 2 H), 6.90 (t, 1 H, J=1.6 Hz), 5.38 (dd, 1 H, J=12.0 , 4.8 Hz), 3.30 (ddd, 1 H, J=18.0, 12.0, 1.6 Hz), 2.68 (ddd, 1 H, J=18.0, 4.8, 1.6 Hz), 1.83 (qd, 2 H, J=7.6, 3.2 Hz), 1.27 (s, 3 H,), 1.25 (s, 3 H,) 0.78 (t, 3 H, J=7.2 Hz). LC-MS (ESI) [M+H]$^+$ calad for $C_{15}H_{20}N_2O$, 245.2; found, 245.2

Compound 21: Preparation of 2,2-dimethyl-1-(5-phenylpyrazolidin-1-yl)butan-1-one

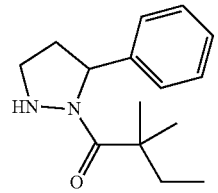 [SMILES: CCC(C)(C)C(=O)N1NCCC1c1ccccc1]

To a solution of compound 20 (40 mg) in dry tetrahydrofuran (5 ml) was added drop wise a solution of lithium triethylborohydrate (1M in tetrahydrofuran) under nitrogen at 0° C. The mixture was stirred at 0° C. for 2 h and quenched with 2M sodium hydroxide (2 ml). The solvent was evaporated to dryness and the residue was extracted with dichloromethane. The extracts were washed with 2M sodium hydroxide solution and concentrated. The residue was purified by column chromatography to give compound 21 (23 mg, 56%). $^1$H NMR (CDCl$_3$, 400 MHz): δ7.27-7.35 (m, 4 H), 7.22-7.26 (m, 1 H), 5.39-5.43 (m, 1 H), 3.34-3.38 (m, 1 H), 2.71-2.77 (m, 1 H), 2.01-2.10 (m, 1 H), 1.72-1.80 (m, 1 H), 1.50-1.55 (m, 2 H), 1.22 (s, 3 Hz), 1.24 (s, 3 Hz), 0.84 (t, 3 H, J=7.2 Hz). LC-MS (ESI) [M+H]$^+$ calad for $C_{15}H_{22}N_2O$, 247.1; found, 247.1.

Compound 22: Preparation of 2,2-dimethyl-1-(2-methyl-5-phenylpyrazolidin-1-yl)butan-1-one

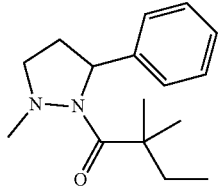 [SMILES: CCC(C)(C)C(=O)N1C(c2ccccc2)CCN1C]

Compound 21 (10 mg), cesium carbonate (26.5 mg) and iodomethane (11.5 mg) in N,N-dimethylformamide (1 ml) were carried out in a Biotage Initiator microwave synthesizer, which was programmed to heated up to 110° C. and stirred for 90 min. Then the mixture was concentrated in vacuo. The residue was purified by flash chromatography on silica gel to give compound 156 (4 mg, 38%). $^1$HNMR (CDCl$_3$, 400 MHz): δ 7.25-7.32 (m, 4 H), 7.18-7.22 (m, 1 H), 5.38 (t, 1 H, J=8.8 Hz), 2.94-3.05 (m, 2 H), 2.58-2.65 (m, 1 H), 2.56 (s, 3 H), 2.32-2.38 (m, 1 H), 1.76-1.89 (m, 2 H), 1.30 (s, 3 H), 1.28 (s, 3 H), 0.92 (t, 3 H, J=7.6 Hz). LC-MS (ESI) [M+H]$^+$ calad for C16H24N2O, 261.2; found 261.2.

Compound 23: Preparation of (R)-3-(2,2-dimethylbutanoyl)-4-phenyloxazolidin-2-one

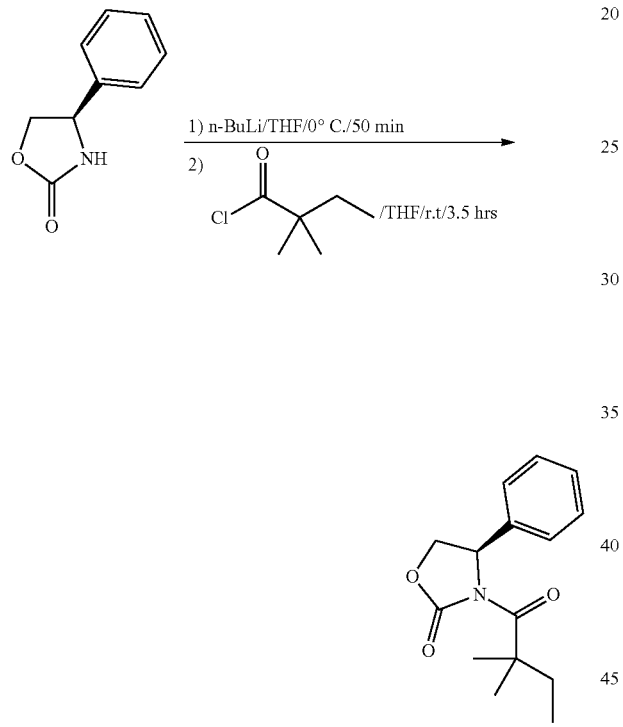

n-BuLi (2.4 M in THF, 0.214 mL, 0.51 mmol) was added slowly to a solution of (R)-4-phenyloxazolidin-2-one (80 mg, 0.49 mmoL) in 2 mL of THF at 0° C. under nitrogen, which was stirred at 0° C. for 50 min. Then 2,2-dimethylbutanoyl chloride (78.9 mg, 0.59 mmol) was added slowly to the solution at 0° C. The mixture was allowed to stir at room temperature for 3.5 h and quenched with saturated aqueous solution of NH$_4$Cl. The aqueous layer were extracted with EtOAc (5 mL×3). The combined organic layers were washed with water and brine, dried with Na$_2$SO$_4$, filtered and concentrated. The residue was crystallized with petroleum ether at −20° C. to give 31 mg of compound 23 as white solid (yield=24.2%). $^1$H NMR (CDCl$_3$, 400 MHz): δ (ppm) 7.29-7.40 (m, 5 H), 5.48 (dd, 1 H, J=4.8, 8.4 Hz), 4.67 (t, 1 H, J=8.4 Hz), 4.23 (dd, 1 H, J=4.8, 8.4 Hz), 1.77-1.95 (m, 2 H), 1.31 (s, 3 H), 1.29 (s, 3 H), 0.70 (t, 3 H, J=7.2 Hz). LC-MS (ESI) [M+H]$^+$ calad for C$_{15}$H$_{19}$NO$_3$, 262.1; found 262.2.

Compound 24: Preparation of (S)-1-(2,2-dimethylbutanoyl)-4-phenylazetidin-2-one

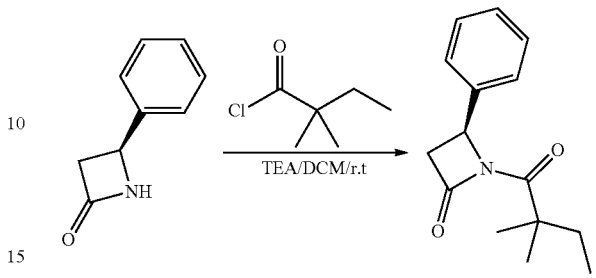

(S)-4-phenylazetidin-2-one (60 mg, 0.41 mmoL) and triethylamine (189.5 mg, 1.9 mmol) were dissolved in 2 mL of dry dichloromethane. The mixture was cooled to 0° C. and 2,2-dimethylbutanoyl chloride (60.1 mg, 0.448 mmol) was added, then allowed to warm to room temperature and stirred for 16 h. The mixture was diluted with water and the aqueous layer was extracted with dichloromethane. The extracts were washed with brine, dried with Na$_2$SO$_4$, filtered and concentrated. The residue was purified by column chromatography(ethyl acetate/petroleum ether=1/5) to give compound 24 (50 mg, 50%) as colorless oil. $^1$H NMR (CDCl$_3$, 400 MHz): δ (ppm) 7.34-7.38 (m, 2 H), 7.29-7.33 (m, 3 H), 4.94 (dd, 1 H, J=3.2 Hz, J=6.8 Hz), 3.38 (dd, 1 H, J=6.8 Hz, J=16.4 Hz), 2.84 (dd, 1 H, J=3.2 Hz, J=16.4 Hz), 1.84 (q, 2 H, J=7.6 Hz), 1.26 (s, 6 H), 0.80 (t, 3 H, J=7.6Hz). LC-MS (ESI) [M+H]$^+$ calad for C$_{15}$H$_{19}$NO$_2$, 246.1; found 246.2

Compound 25: Preparation of 4-(3-azidophenyl)-1-(2,2-dimethylbutanoyl)azetidin-2-one

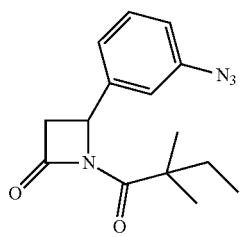 [SMILES: CCC(C)(C)C(=O)N1C(=O)CC1c1cccc(N=[N+]=[N-])c1]

A solution of 1-azido-3-vinylbenzene (200 mg) in absolute toluene (3 ml) was added drop wise to a stirred solution of chlorosulfonyl isocyanate (119 ul) in absolute toluene (3 ml) at 0° C. The mixture was stirred at room temperature for 8 h and then left to stand overnight. The solution was added drop wise to a vigorously stirred solution of sodium sulfite (87 mg) and sodium carbonate (73 mg) in water (1 ml). The layer were separated and the aqueous was extracted with toluene. The combined organic layers were dried with Na$_2$SO$_4$, filtered and concentrated and the residue was washed with diethyl ether to give 4-(3-azidophenyl)azetidin-2-one (100 mg). $^1$H NMR (CDCl$_3$, 400 MHz) : 7.36 (t, J=7.76 Hz, 1H), 7.11-7.17 (m, 1H), 6.18-7.01 (m, 2H), 4.72(dd, J=2.4, 5.2 Hz, 1H), 3.43-3.49 (m, 1H), 2.84-2.88 (m, 1H).

The above intermediate (30 mg) and triethylamine (27 uL) were dissolved in dichloromethane (4 mL). The mixture was cooled to 0° C. and 2,2-dimethylbutanoylchloride (26 mg) was added. The mixture was allowed to warm to room temperature and stirred for 2 h, and diluted with water. The aqueous layer was extracted with dichloromethane. The combined organic layers was washed with water and brine, dried with (Na$_2$SO$_4$) and concentrated. The residue was purified by silica gel column chromatography(ethyl acetate/ petroleum ether=1/4) to give the desired product (35 mg, 48%) as an white solid. $^1$H NMR (CDCl$_3$, 400 MHz): δ7.33-7.37 (m, 1 H), 7.06-7.09 (m, 1 H), 6.93-6.99 (m, 2 H), 4.92 (dd, 1 H, J=3.2 , 6.4 Hz), 3.39 (dd, 1 H, J=6.4, 16.4 Hz), 2.81 (dd, 1 H, J=3.2, 16.4 Hz), 1.846 (qd, 2 H, J=1.2, 7.6 Hz), 1.27 (s, 3 H), 1.26 (s, 3 H), 0.82 (t, 3 H, J=7.6 Hz). LC-MS (ESI) [M+H]$^+$ calad for C$_{15}$H$_{18}$N$_4$O$_2$, 287.1; found, 287.2.

Compound 26: Preparation of 4-(3-bromophenyl)-1-(2,2-dimethylbutanoyl)azetidin-2-one

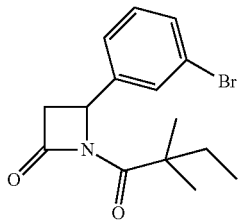 [SMILES: CCC(C)(C)C(=O)N1C(=O)CC1c1cccc(Br)c1]

Compound 26 was prepared in 51% from 4-(3-bromophenyl) azetidin-2-one (200 mg) and 2,2-dimethylbutanoyl chloride (147 mg) according to the procedure outlined for compound 25. $^1$H NMR (CDCl$_3$, 400 MHz): δ7.41-7.47 (m, 2 H), 7.23-7.24 (m, 2 H), 4.89 (dd, 1 H, J=3.6, 6.4 Hz), 3.39 (dd, 1 H, J=6.4, 16.4 Hz), 2.81 (dd, 1 H, J=3.6, 16.4 Hz), 1.84 (q, 2 H, J=7.2 Hz), 1.26 (s, 6 H), 0.82 (t, 3 H, J=7.2 Hz). LC-MS (ESI) [M+H]$^+$ calad for C$_{15}$H$_{18}$BrNO$_2$, 324.1; found 324.2, 326.2.

Compound 172: Preparation of 1-(2,2-dimethylbutanoyl)-4-(3-ethynylphenyl)azetidin-2-One

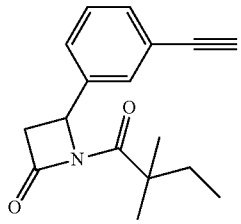 [SMILES: C#Cc1cccc(C2CC(=O)N2C(=O)C(C)(C)CC)c1]

To solution of compound 26 (165 mg) and triphenylphosphine (13 mg) in dry triethylamine (4 ml) was added ethynyltrimethylsilane (87 ul) and palladium acetate (6 mg) The mixture was heated to reflux for 4 h, cooled to room temperature and filtered. The filtrate was concentrated under vacuum to a thick oil, which was purified by column chromatography (acetic ether/petroleum=1/10) to give 1-(2, 2-dimethylbutanoyl)-4-(3-((trimethylsilyl)ethynyl)phenyl) azetidin-2-one (140 mg, 80%) as a yellow solid. $^1$H NMR (CDCl$_3$, 400 MHz): 7.38-7.42 (m, 2H), 7.22-7.31 (m, 2 H), 4.90 (dd, J=3.2, 6.8 Hz, 1H), 3.37 (dd, J=6.8, 16.4 Hz, 1H), 2.82 (dd, J=3.2, 16.4 Hz, 1H), 1.95-1.73 (m, 2H), 1.26 (s, 6H), 0.81 (t, J=7.6 Hz, 3H), 0.24 (s, 9H).

The above intermediate (60 mg) was dissolved in tetrahydrofuran (3 ml), then tetrabutyl ammonium fluoride (51 mg) was added to the solution at 0° C. The mixture was stirred at 0° C. for 3 h. After completion of the reaction, H$_2$O (3 ml) was added and extracted with CH$_2$Cl$_2$. The combined organic layers was washed with water and brine, dried with (Na$_2$SO$_4$) and concentrated. The residue was purified by silica gel column chromatography to give compound 27(11 mg, 23%). $^1$H NMR (CDCl$_3$, 400 MHz): δ7.42-7.44 (m, 2 H), 7.28-7.34 (m, 2 H), 4.91 (dd, 1 H, J=3.2, 6.4 Hz), 3.39 (dd, 1 H, J=6.4, 16.4 Hz), 3.08 (s, 1 H), 2.82 (dd, 1 H, J=3.2, 16.4 Hz), 1.84 (q, 2 H, J=7.2 Hz), 1.26 (s, 6 H), 0.81 (t, 3 H, J=7.2 Hz). MS(ES) [M+H]$^+$ calad for C$_{17}$H$_{19}$NO$_2$, 270.1; found, 270.3.

Compound 28: Preparation of 1-(2,2-dimethylbutanoyl)-4-(3-nitrophenyl)azetidin-2-one

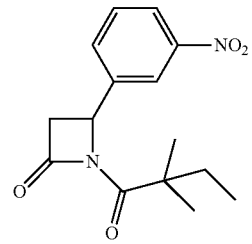 [SMILES: CCC(C)(C)C(=O)N1C(=O)CC1c1cccc([N+](=O)[O-])c1]

Compound 28 was prepared in 25% yield from 4-(3-nitrophenyl)azetidin-2-one (10 mg) (prepared form 1-nitro-3-vinylbenzene (200 mg) and chlorosulfonyl isocyanate (116 ul) according to the procedure outlined for compound 170) and 2,2-dimethylbutanoyl chloride (179 mg) according to the procedure outlined for compound 25. $^1$H NMR (CDCl$_3$, 400 MHz): δ 8.18-8.20 (m, 2 H), 7.64-7.66 (m, 1 H), 7.55-7.59 (m, 1 H), 5.04 (q, 1 H, J=3.6 , 6.4Hz), 3.48 (dd, 1 H, J=6.4, 16.4 Hz), 2.87 (dd, 1 H, J=3.6, 16.4 Hz), 1.82-1.89 (m, 2 H), 1.27 (s, 6 H), 0.82 (t, 3 H, J=7.6 Hz). MS(ES) [M+H]$^+$ calad for C$_{15}$H$_{18}$N$_2$O$_4$, 290; found, 291.

Compound 29: Preparation of 1-(2,2-dimethylbutanoyl)-5-phenylpyrrolidin-2-one

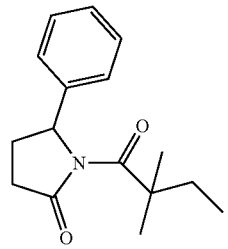 [SMILES: CCC(C)(C)C(=O)N1C(=O)CCC1c1ccccc1]

The titled compound 29 was prepared in 38% yield from 5-phenylpyrrolidin-2-one (50 mg) and 2,2-dimethylbutanoyl chloride (50 mg) according to the procedure outlined for compound 1. $^1$HNMR (CDCl$_3$, 400 MHz): δ7.27-7.35 (m, 2 H), 7.20-7.25 (m, 3 H), 5.379 (dd, 1 H, J=4.4 Hz, J=8.0 Hz), 2.70-2.79 (m, 1 H), 2.42-2.60 (m, 2 H), 1.87-2.00 (m, 2 H), 1.64-1.73 (m, 1 H), 1.30 (s, 3 H), 1.24 (s, 3 H), 0.68(t, 3H, J=7.6Hz). MS(ES) [M+H]⁺ calad for $C_{16}H_{21}NO_2$, 260.2; found, 260.3.

Compound 30: Preparation of (R)-3-(2,2-dimethylbutanoyl)-4-phenyl-1-(prop-2-yn-1-yl)imidazolidin-2-one

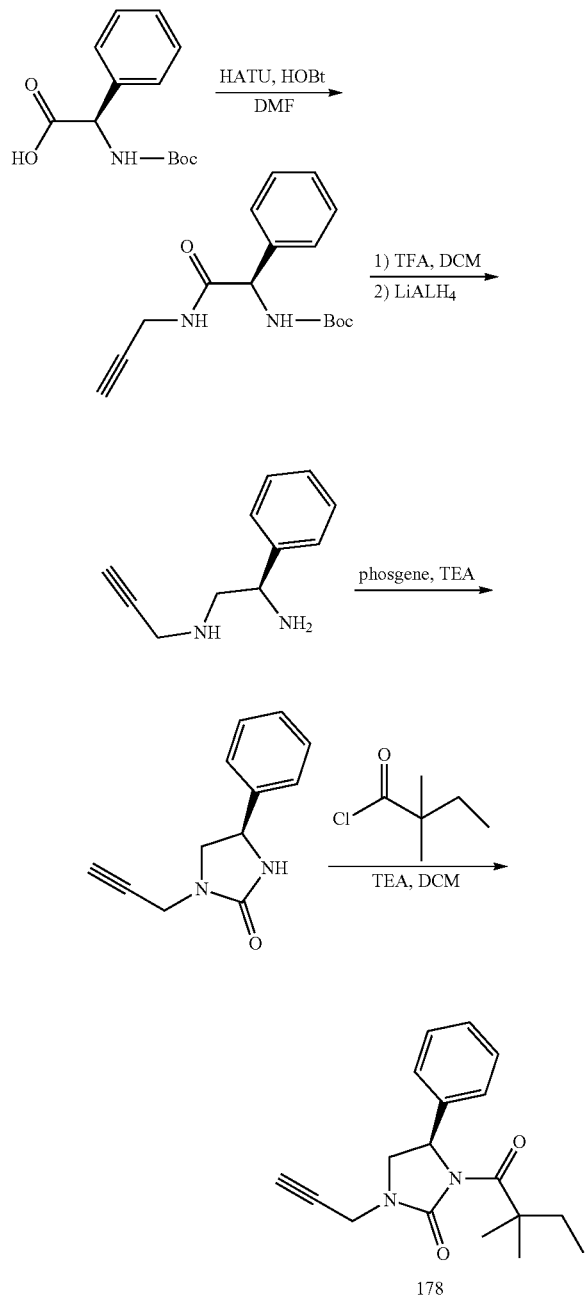

The above compound (500 mg) was dissolved in $CH_2Cl_2$ (8 ml), TFA (2 ml) was added. The mixture was stirred for 4 h and concentrated. After standard work up, the resulting crude product: (R)-2-amino-2-phenyl-N-(prop-2-yn-1-yl) acetamide (240 mg) was added to a solution of lithium aluminum hydrate (194 mg) in THF (5 ml) at 0° C. and stirred for 1 h, then the mixture was refluxed for 2 h, added 0.2 ml of water, 0.2 ml of 15% NaOH and 0.2 ml water in this order, filtered and evaporated. The resulting yellow liquid (130 mg) was used for next step without further purification.

The above compound: (R)-1-phenyl-N2-(prop-2-yn-1-yl) ethane-1,2-diamine(130 mg) and triethylamine (0.5 ml) were dissolved in dry THF (30 ml), phosgene (118 mg) was added at 0° C. and stirred for overnight. The mixture was diluted with dichloromethane and water. The aqueous layer was extracted with dichloromethane. The combined organic layers was washed with water and brine, dried ($Na_2SO_4$) and concentrated in vacuo. The residue was purified by column chromatography to give 150 mg of (R)-4-phenyl-1-(prop-2-yn-1-yl)imidazolidin-2-one The above intermediate (150 mg) and triethylamine (0.16 ml) were dissolved in dry dichloromethane (2 ml). The mixture was cooled to 0° C. and 2,2-dimethylbutanoylchloride (120 mg) was added, then allowed to warm to room temperature and stirred for 16 h. The mixture was diluted with dichloromethane and water. The aqueous layer was extracted with dichloromethane. The organic layers were combined and concentrated. The residue was purified by column chromatography to give compound 30 (50 mg, total yield 10%) as colorless oil. ¹H NMR (CDCl₃, 400 MHz): δ7.27-7.35 (m, 5 H), 5.37 (dd, 1 H, J=3.6, 9.2 Hz), 4.12-4.13 (m, 2 H), 3.91 (t, 1 H, J=9.2 Hz), 3.32 (dd, 1 H, J=3.6, 9.2 Hz), 2.27 (t, 1 H, J=2.4 Hz), 1.89 (dq, 2 H, J=1.6, 7.6 Hz), 1.28 (s, 3 H), 1.29 (s, 3 H), 0.70 (t, 3 H, J=7.6 Hz). MS(ES) [M+H]⁺ calad for $C_{18}H_{22}N_2O_2$, 299.2; found, 299.3.

Compound 31: Preparation of (R)-3-(2,2-dimethylbutanoyl)-1-methyl-4-phenylimidazolidin-2-one

178

(R)-tert-butyl (2-oxo-1-phenyl-2-(prop-2-yn-1-ylamino) ethyl)carbamate was prepared from (R)-2-((tert-butoxycarbonyl)amino)-2-phenylacetic acid and prop-2-yn-1-amine according to the procedure for compound 53. ¹H NMR (CDCl₃, 400 MHz): δ7.32-7.36 (m, 5H), 6.03 (brs, 1H), 5.73 (brs, 1H), 5.15 (brs, 1H), 3.93-4.12 (m, 2H), 2.20 (t, J=2.8 Hz), 1.41 (s, 9H).

The titled compound 31 was prepared from (R)-3-(2,2-dimethylbutanoyl)-1-methyl-4-phenylimidazolidin-2-one (50 mg) and 2,2-dimethylbutanoyl chloride (45 mg) according to the procedure outlined for compound 1. ¹H NMR (CDCl₃, 400 MHz): δ7.31-7.35 (m, 2 H), 7.24-7.30 (m, 3 H), 5.33 (dd, 1 H, J=4.0, 9.2 Hz), 3.813 (t, 1 H, J=9.2 Hz), 3.20 (dd, 1 H, J=4.0, 9.2 Hz), 2.900 (s, 3 H), 1.92 (m, 2 H), 1.31 (s, 3H), 1.29 (s, 3H), 0.73 (t, 3 H, J=7.2 Hz). MS(ES) [M+H]⁺ calad for $C_{16}H_{22}N_2O_2$, 275.2; found 275.4.

Compound 32: Preparation of 1-(2,2-dimethylbutanoyl)-3,3-difluoro-4-phenylazetidin-2-one

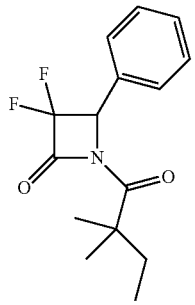 [SMILES: CCC(C)(C)C(=O)N1C(=O)C(F)(F)C1c1ccccc1]

The titled compound 32 was prepared in 60% yield from 3,3-difluoro-4-phenylazetidin-2-one (30 mg) and 2,2-dimethylbutanoyl chloride (44 mg) according to the procedure outlined for compound 164. $^1$H NMR (CDCl$_3$, 400 MHz): δ7.39-7.43 (m, 3 H), 7.24-7.27 (m, 2 H), 5.35 (dd, 1 H, J=3.2, 10.4 Hz), 1.79-1.92 (m, 2 H), 1.32 (s, 3 H), 1.30 (s, 3 H), 0.86 (t, 3 H, J=7.6 Hz). MS(ES) [M+H]$^+$ calad for C$_{15}$H$_{17}$F$_2$NO$_2$, 282.1; found, 282.3.

Compound 33: Preparation of 2-(2,2-dimethylbutanoyl)-1-phenylpyrazolidin-3-one

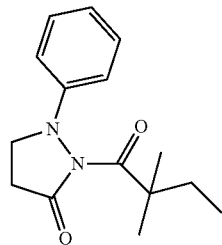 [SMILES: CCC(C)(C)C(=O)N1C(=O)CCN1c1ccccc1]

The titled compound 33 was prepared in 25% yield from phenylpyrazolidin-3-one (50 mg) and 2,2-dimethylbutanoyl chloride (50 mg) according to the procedure outlined for compound 1. $^1$HNMR (CDCl$_3$, 400 MHz): δ7.19-7.35 (m, 2 H), 6.97-7.07 (m, 2 H), 6.85 (t, 1 H, J=8.0 Hz), 3.916 (t, 2 H, J=8.0 Hz), 3.14 (t, 2 H, J=8.0 Hz), 1.69 (q, 2 H, J=7.6 Hz), 1.28 (s, 6 H), 0.93 (t, 3 H, J=7.6 Hz). MS(ES) [M+H]$^+$ calad for C$_{15}$H$_{20}$N$_2$O$_2$, 261.2; found, 261.3.

Compound 34: Prepared of 1-(2,2-dimethylbutanoyl)-5-phenylpyrazolidin-3-one

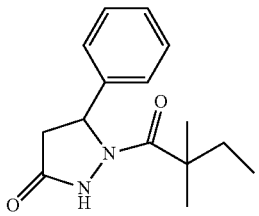 [SMILES: CCC(C)(C)C(=O)N1NC(=O)CC1c1ccccc1]

To a solution of 5-phenylpyrazolidin-3-one (65 mg) and triethylamine (0.066 ml) in dry tetrahydrofuran (4 ml) was slowly added 2,2-dimethylbutanoyl chloride (0.06 ml) at 0° C. under nitrogen. Then the mixture was allowed to warm to room temperature and stirred for 2 h. The mixture was diluted with water and the aqueous layer was extracted with dichloromethane. The combined organic layers were washed with brine, dried (Na$_2$SO$_4$) and concentrated. The residue was purified by column chromatography (ethyl acetate/petroleum ether=1/3) to give 1,1'-(3-oxo-5-phenylpyrazolidine-1,2-diyl)bis(2,2-dimethylbutan-1-one) (50 mg, 34%) as an white solid.

The above intermediate (10 mg) was dissolved in tetrahydrofuran (1 ml) and 1M sodium hydroxide (0.05 ml) was added. The mixture was stirred for 2 h and diluted with dichloromethane and water. The aqueous layer was extracted with dichloromethane. The combined organic was washed with brine, dried with Na$_2$SO$_4$ and concentrated. The residue was purified by silica gel column chromatography (ethyl acetate/petrol-eumether=1/2) to give compound 34 (5.1 mg, 69%) as a white solid. $^1$H NMR (CDCl$_3$, 400 MHz): δ7.28-7.40 (m, 5 H), 5.82 (d, 1 H, J=9.6 Hz), 3.34 (dd, 1 H, J=9.6 , 16.4 Hz), 2.60 (d, 1 H, J=16.4 Hz), 1.57 (q, 2 H, J=7.6 Hz), 1.17 (s, 3 H), 1.14 (s, 3 H), 0.81 (t, 3 H, J=7.6 Hz). LC-MS (ESI) [M+H]$^+$ calad for C$_{15}$H$_{20}$N$_2$O$_2$, 261.2; found, 261.3.

Compound 35: Preparation of (2-(3-fluorophenyl)pyrrolidin-1-yl)(1-(trifluoromethyl)cyclopentyl)methanone 2-(3-fluorophenyl)pyrrolidine (9 mg), which was prepared according the literature reported procedures, and 1-(trifluoromethyl)cyclopentanecarboxylic acid (10 mg) were dissolved in dry DMF (1 ml). 2-(7-Aza-1H-benzotriazole-1-yl)-1,1,3,3-tetramethyluronium hexafluorophosphate (31 mg) and N,N-Diisopropylethylamine (14 mg) were added to the solution. The mixture was stirred at room temperature for 16 h. The solvent was removed under reduced pressure and the residue was purified by column chromatography to give
the desired product (8 mg, 44.2%). $^1$H NMR: (CDCl$_3$, 400 MHz): δ7.24-7.28 (m, 1 H), 6.87-6.92 (m, 2 H), 6.79-6.82 (m, 1 H), 5.16-5.19 (m, 1 H), 3.90-3.96 (m, 1 H), 3.73-3.79 (m, 1 H), 2.46-2.50 (m, 1 H), 2.28-2.36 (m, 2 H), 2.09-2.19 (m, 2 H), 1.95-2.06 (m, 1 H), 1.83-1.93 (m, 1 H), 1.64-1.78 (m, 5 H). LC-MS (ESI) [M+H]$^+$ calad for C$_{17}$H$_{19}$F$_4$NO, 330.1; found 3303.

Compound 36: Preparation of (2-(3-fluorophenyl) pyrrolidin-1-yl)(1-(trifluoromethyl)cyclobutyl) methanone

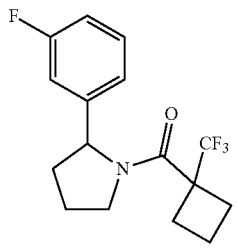 [SMILES: O=C(N1CCCC1c1cccc(F)c1)C1(C(F)(F)F)CCC1]

The titled compound 36 was prepared in 32% yield from 1-(trifluoromethyl)cyclobutanecarboxylic acid (20 mg) and 2-(3-fluorophenyl)pyrrolidine (19.6 mg) according to the procedure outlined for compound 35. $^1$H NMR: (CDCl$_3$, 400 MHz): δ7.23-7.29 (m, 1 H), 6.81-6.95 (m, 3 H), 5.13-5.16 (m, 1 H), 3.58-3.70 (m, 2 H), 2.71-2.82 (m, 1 H), 2.59-2.67 (m, 1 H), 2.41-2.56 (m, 2 H), 2.31-2.39 (m, 1 H), 2.08-2.18 (m, 1 H), 1.95-2.05 (m, 1 H), 1.76-1.92 (m, 3 H). LC-MS (ESI) [M+H]$^+$ calad for C$_{16}$H$_{17}$F$_4$NO, 316.1; found 316.3.

Compound 37: Preparation of adamantan-1-yl(2-(3-fluorophenyl)pyrrolidin-1-yl)methanone

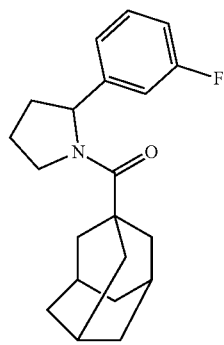 [SMILES: O=C(N1CCCC1c1cccc(F)c1)C12CC3CC(CC(C3)C1)C2]

The titled compound 37 was prepared in 46% yield from 2-(3-fluorophenyl)pyrrolidine (60 mg) and adamantane-1-carbonyl chloride (81 mg) according to the procedure outlined for compound 1. $^1$HNMR (CDCl$_3$, 400 MHz): δ7.21-7.26 (m, 1 H), 6.78-6.92 (m, 3 H), 3.91 (m, 2 H), 2.17-2.26 (m, 1 H), 1.89-1.20 (m, 10 H), 1.71-1.76 (m, 8 H). LC-MS (ESI) [M+H]$^+$ calad for C$_{21}$H$_{26}$FNO, 328.2; found, 328.4.

Compound 38: Preparation of (S)-1-(2,2-dimethyl-but-3-enoyl)-4-phenylazetidin-2-one

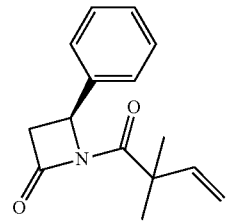 [SMILES: C=CC(C)(C)C(=O)N1C(=O)C[C@H]1c1ccccc1]

The titled compound 38 was prepared in 34% yield from (S)-4-phenylazetidin-2-one (100 mg) and 2,2-dimethylbut-3-enoyl chloride (107 mg) according to the procedure outlined for compound 1. $^1$H NMR (CDCl3, 400 MHz): δ 7.27-7.39 (m, 5 H), 6.26 (dd, 1 H, J=10.8, 17.2 Hz), 5.18 (dd, 1 H, J=0.8, 10.8 Hz), 5.12 (d, 1 H, J=0.8, 17.2 Hz), 4.94 (dd, 1 H, J=3.6, 6.4 Hz), 3.39 (dd, 1 H, J=6.4, 16.4 Hz), 2.82 (dd, 1 H, J=3.6, 16.4 Hz), 1.41 (s, 3 H), 1.39 (s, 3 H). LC-MS (ESI) [M+H]+ calad for C15H17NO2, 244.1; found, 244.3.

Compound 39: Preparation of (R)-3-acetyl-4-phenyloxazolidin-2-one

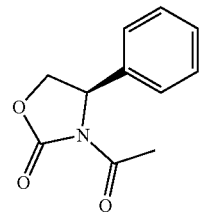

The titled compound 39 was prepared in 60% yield from (R)-4-phenyloxazolidin-2-one (80 mg) and acetyl chloride (46 mg) according to the procedure outlined for compound 1. $^1$H NMR (CDCl$_3$, 400 MHz): δ7.29-7.41 (m, 5 H), 5.425 (dd, 1 H, J=3.6, 8.8 Hz), 4.69 (t, 1 H, J=8.8 Hz), 4.29 (dd, 1 H, J=3.6, 8.8 Hz), 1.53 (s, 3 H). LC-MS (ESI) [M+H]$^+$ calad for C$_{11}$H$_{11}$NO$_3$, 206.1; found, 206.2.

Compound 40: Preparation of (S)-1-(3-chloroacryloyl)-4-phenylazetidin-2-one

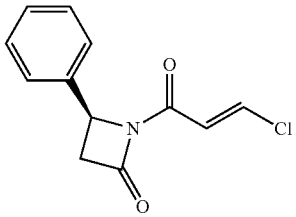 [SMILES: O=C(/C=C/Cl)N1C(=O)C[C@H]1c1ccccc1]

A solution of (S)-4-phenylazetidin-2-one (40 mg, 0.272 mmoL) and DIEA (35.1 mg, 0.272 mmoL) in 0.5 mL of CH$_2$Cl$_2$ was added slowly to a mixture of 3-chloroacryloyl chloride (37.1 mg, 0.299 mmoL) and DIEA (38.6 mg, 0.299 mmoL) in 1.5 mLof CH$_2$Cl$_2$ at 0° C. The mixture was allowed to stir at room temperature for 16 h. After removing of solvents and the brown residue was purified by preparative TLC plate to give 0.4 mg of compound 40 as brown oil (yield=0.6%). $^1$H NMR: (CDCl$_3$, 400 MHz) δ7.31-7.40 (m, 5 H), 7.14 (d, 1 H, J=8.0 Hz), 6.83 (d, 1 H, J=8.0 Hz), 5.11 (dd, 1 H, J=3.6, 6.4 Hz), 3.53 (dd, 1 H, J=6.4, 16.4 Hz), 3.03 (dd, 1 H, J=3.6, 16.4 Hz). LC-MS (ESI) [M+H]$^+$ calad for Cl$_2$H$_{10}$ClNO$_2$, 236.0; found, 236.2.

Compound 41: Prepared of (4S)-1-(tert-butylsulfinyl)-4-phenylazetidin-2-one

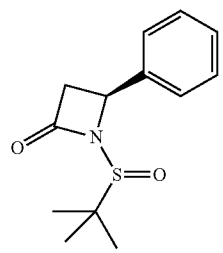 [SMILES: CC(C)(C)S(=O)N1C(=O)C[C@H]1c1ccccc1]

To a solution of (S)-4-phenylazetidin-2-one (50 mg) and triethylamine (0.1 mL) in dry THF (2 mL) was slowly added 2-methylpropane-2-sulfinic chloride (50 ul) at 0° C. under nitrogen. The mixture was allowed to warm to room temperature and stirred for 2 h. The mixture was diluted with dichloromethane and water. The aqueous layer was extracted with dichloromethane and the combined organic layers were washed with brine, dried (Na$_2$SO$_4$) and concentrated. The residue was purified by silica gel column chromatography (ethyl acetate/petroleum ether=1/5) to give compound 167 (20 mg, 24%) as an white solid. $^1$H NMR (CDCl$_3$, 400 MHz): δ7.33-7.46 (m, 5 H), 5.12 (dd, 1 H, J=3.6, 6.8 Hz), 3.60 (dd, 1 H, J=16.0, 6.8 Hz), 3.21 (dd, 1 H, J=16.0, 3.6 Hz), 0.98 (s, 9 H). LC-MS (ESI) [M+H]$^+$ calad for C$_{13}$H$_{17}$NO$_2$S, 252.1; found 252.2.

Compound 42: Prepared of (S)-1-(isopropylsulfonyl)-4-phenylazetidin-2-one

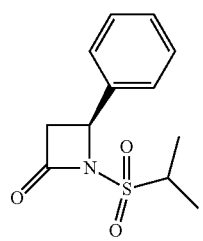 [SMILES: CC(C)S(=O)(=O)N1C(=O)C[C@H]1c1ccccc1]

The titled compound 42 was prepared in 34% yield from (S)-4-phenylazetidin-2-one (50 mg) and propane-2-sulfonyl chloride (58 mg) according to the procedure outlined for compound 23. $^1$H NMR (CDCl$_3$, 400 MHz): δ7.37-7.46 (m, 5 H), 5.20 (dd, 1 H, J=3.2, 6.4 Hz), 3.61 (dd, 1 H, J=6.4, 16.0 Hz), 3.17 (dd, 1 H, J=3.2, 16.0 Hz), 2.93-3.00 (m, 1 H), 1.29 (d, 3 H, J=3.2 Hz), 1.27 (d, 3 H, J=3.2 Hz). LC-MS (ESI) [M+H]$^+$ calad for C$_{12}$H$_{15}$NO$_3$S , 254.1; found 254.2.

Compound 43: Prepared of (S)-1-(ethylsulfonyl)-4-phenylazetidin-2-one

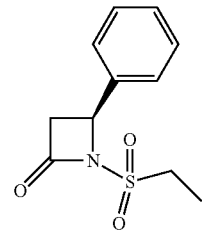 [SMILES: CCS(=O)(=O)N1C(=O)C[C@H]1c1ccccc1]

The titled compound 43 was prepared in 33% yield from (S)-4-phenylazetidin-2-one (50 mg) and ethanesulfonyl chloride (52.5 mg) according to the procedure outlined for compound 23. $^1$H NMR (CDCl$_3$, 400 MHz): 7.37-7.45 (m, 5 H), 5.19 (dd, 1 H, J=3.6, 6.4 Hz), 3.61 (dd, 1 H, J=6.4, 16.4 Hz), 3.16 (dd, 1 H, J=3.6, 16.4 Hz), 2.80 (q, 2 H, J=7.2 Hz), 1.31 (t, 3 H, J=7.2 Hz). LC-MS (ESI) [M+H]$^+$ calad for C$_{11}$H$_{13}$NO$_3$S, 240.1; found 240.2

Compound 44: Preparation of 4-(3-azidophenyl)-1-(2,2-dimethylbut-3-ynoyl)azetidin-2-one

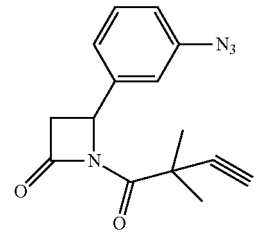 [SMILES: C#CC(C)(C)C(=O)N1C(=O)CC1c1cccc(N=[N+]=[N-])c1]

Compound 44 was prepared in 1.3% yield from 4-(3-azidophenyl)azetidin-2-one (50mg) (prepared according to the procedure outlined for compound 25) and 2,2-dimethylbut-3-ynoyl chloride (69 mg) according to the procedure outlined for compound 24. $^1$H NMR (CDCl$_3$, 400 MHz): δ 7.34-7.38 (m, 1 H), 7.09-7.11 (m, 1 H), 6.97-7.00 (m, 2 H), 4.98 (dd, 1 H, J=3.2, 6.8 Hz), 3.48 (dd, 1 H, J=6.8, 16.4 Hz), 2.88 (dd, 1 H, J=3.2, 16.4 Hz), 2.35 (s, 1 H), 1.59 (s, 3 H), 1.57 (s, 3 H). MS(ES) [M+H]$^+$ calad for C$_{15}$H$_{14}$N$_4$O$_2$, 283.1; found, 283.3.

Compound 45: Prepared of (S)-1-(tert-butylsulfonyl)-4-phenylazetidin-2-one

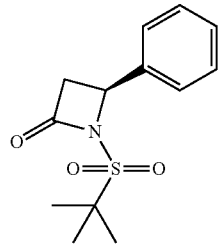 [SMILES: CC(C)(C)S(=O)(=O)N1C(=O)C[C@H]1c1ccccc1]

To a solution of compound 41 (9 mg) in dichloromethane (4 ml) was added m-CPBA (12.3 mg). The mixture was stirred at room temperature for 16 h and diluted with water. The aqueous layer was extracted with dichloromethane and the combined organic layers was washed with brine, dried ($Na_2SO_4$) and concentrated. The residue was purified by preparation TLC plate(ethyl acetate/petroleum ether=1/3) to give compound 45 (5 mg, 52%) as an white solid. $^1$H NMR ($CDCl_3$, 400 MHz): δ7.34-7.47 (m, 5 H), 5.24 (dd, 1 H, J=3.6, 6.4 Hz), 3.61 (dd, 1 H, J=6.4, 16.4 Hz), 3.238 (dd, 1 H, J=3.6 , 16.4 Hz), 1.20 (s, 9 H). LC-MS (ESI) $[M+H]^+$ calad for $C_{13}H_{17}NO_3S$, 268.1; found 268.2.

Compound 46: Preparation of (S)-2,2-dimethyl-1-(2-phenylazetidin-1-yl)but-3-yn-1-one

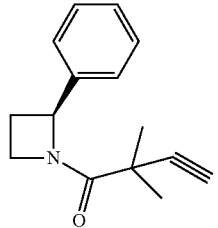 [SMILES: C#CC(C)(C)C(=O)N1CC[C@H]1c1ccccc1]

Compound 46 was prepared in 13% yield from (S)-2-phenylazetidine (50 mg) and 2,2-dimethylbut-3-ynoic acid (69 mg) according to the procedure outlined for compound 35. $^1$HNMR ($CDCl_3$, 400 MHz): δ7.34-7.37 (m, 5 H), 5.35-5.39 (dd, 1 H, J=6.0, 8.4 Hz), 4.56-4.66 (m, 2 H), 2.70-2.79 (m, 1 H), 2.40 (s, 1 H), 2.11-2.19 (m, 1 H), 1.47 (s, 3 H), 1.45 (s, 3 H). MS(ES) $[M+H]^+$ calad for $C_{15}H_{17}NO$, 228.1; found, 228.1.

Compound 47: Preparation of (S)-1-(adamantane-2-carbonyl)-4-phenylazetidin-2-one

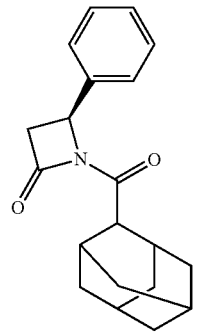

The titled compound 47 was prepared in 32% yield from (S)-4-phenylazetidin-2-one (50 mg) and adamantane-2-carbonyl chloride (81 mg) according to the procedure outlined for compound 24. $^1$H NMR ($CDCl_3$, 400 MHz): δ 7.27-7.38 (m, 5 H), 4.94 (dd, 1 H, J=3.2, 6.8 Hz), 3.37 (dd, 1 H, J=6.8, 16.4 Hz), 2.79 (dd, 1 H, J=3.2, 16.4 Hz), 1.93-2.10 (m, 10 H), 1.72-1.79 (m, 5 H). LC-MS (ESI) $[M+H]^+$ calad for $C_{20}H_{23}NO_2$, 310.2; found, 310.3.

Compound 48: Preparation of(S)-1-ethyl-4-phenylazetidin-2-one

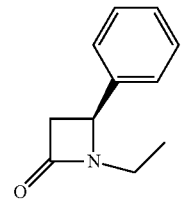

(S)-4-phenylazetidin-2-one (15 mg) was dissolved in 2 mL of dry THF and NaH (5 mg, 60% in material oil) was added in portions at 0° C. under nitrogen. After stirring at 0° C. for 30 min, iodoethane (17.5 mg) was added. The mixture was stirred at room temperature for 16 h, quenched with 1 mL of water and extracted with EtOAc. The extracts were washed with brine, dried with $Na_2SO_4$, filtered and concentrated. The residue was purified by silica gel column chromatography to give 2.6 mg of compound 48 as white solid (14.6%). $^1$H NMR: ($CDCl_3$, 400 MHz): δ7.31-7.41 (m, 5 H), 4.56 (dd, 1 H, J=2.4, 5.2 Hz), 3.43-3.52 (m, 1 H), 3.34 (dd, 1 H, J=5.2 Hz, J=14.4 Hz), 2.90-2.99 (m, 1 H), 2.81 (dd, 1 H, J=2.4 Hz, 14.4 Hz), 1.07 (t, 3 H, J=7.2 Hz). $[M+H]^+$ calad for $C_{11}H_{13}NO$, 176.1; found 176.2.

Compound 49: Preparation of (S)-4-phenyl-1-(prop-2-ynyl)azetidin-2-one

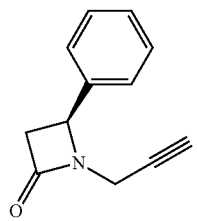

A solution of (S)-4-phenylazetidin-2-one (30 mg, 0.204 mmoL) and 3-iodoprop-1-yne (26.8 mg, 0.227 mmoL) in 2 mL of THF was added drop wise to the mixture of KOH (13.7 mg, 0.245 mmoL) and tetrabutyl ammonium bromide (26.8 mg, 0.227 mmoL) in 2 mL of THF at 0° C. The mixture was allowed to stir at room temperature for 16 h. After filtering, the filtrate was evaporated to dryness and the brown residue was purified by preparative TLC plate (ethyl acetate/petroleum ether=1/4) to give 30 mg of compound 49 as light yellow solid (yield=79.6%). $^1$H NMR ($CDCl_3$, 400 MHz): δ7.28-7.38 (m, 5 H), 6.70 (t, 1 H, J=6.4 Hz), 5.20 (dd, 1 H, J=6.4 ,10.8 Hz), 4.98 (dd, 1 H, J=6.4, 10.8 Hz), 4.69 (dd, 1 H, J=2.8, 5.6 Hz), 3.46 (dd, 1 H, J=5.6, 14.8 Hz), 2.884 (dd, 1 H, J=2.8, 14.8 Hz). LC-MS (ESI) $[M+H]^+$ calad for $C_{12}H_{11}NO$, 186.1; found 186.2.

Compound 50: Preparation of
(S)-1-(cyclopropylmethyl)-4-phenylazetidin-2-one

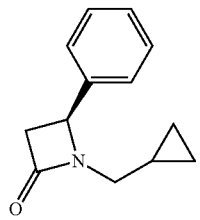 [SMILES: O=C1C[C@@H](c2ccccc2)N1CC1CC1]

The titled compound 50 was prepared in 9.7% yield from (S)-4-phenylazetidin-2-one (15 mg), (bromomethyl)cyclopropane (15 mg) and NaH (4.5 mg, 60% in material oil) according to the procedure outlined for compound 48. $^1$H NMR: (CDCl$_3$, 400 MHz): δ7.31-7.40 (m, 5 H), 4.67 (dd, 1 H, J=2.4, 5.2 Hz), 3.43 (dd, 1 H, J=6.4,14.4 Hz), 3.38 (dd, 1 H, J=5.2, 14.8 Hz), 2.82 (dd, 1 H, J=2.4, 14.8 Hz), 2.57 (dd, 1 H, J=7.6, 14.4 Hz), 0.82-0.88 (m, 1 H), 0.36-0.46 (m, 2 H), 0.01-0.07 (m, 2 H). LC-MS (ESI) [M+H]$^+$ calcd for C$_{13}$H$_{15}$NO, 202.1; found, 202.2.

Compound 51: Preparation of
(R)-3-ethyl-4-phenyloxazolidin-2-one

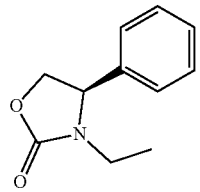

(R)-4-phenyloxazolidin-2-one (50 mg, 0.31 mmoL) was dissolved in 2 mL of dry THF and NaH (15 mg, 0.38 mmoL, 60% in material oil) was added in portions at 0° C. under nitrogen. After stirring at 0° C. for 30 min, iodoethane (57.4 mg, 0.37 mmoL) was added. The mixture was stirred at room temperature for 16 h, quenched with 1 mL of water and extracted with EtOAc. The extracts were washed with brine, dried with Na$_2$SO$_4$, filtered and concentrated. The residue was purified by silica gel column chromatography to give 12 mg of compound 51 as white solid (yield=20.5%). $^1$H NMR: (CDCl$_3$, 400 MHz) δ7.38-7.44 (m, 3 H), 7.30-7.32 (m, 2 H), 4.80 (dd, 1 H, J=7.2, 8.8 Hz), 4.61 (t, 1 H, J=8.8 Hz), 4.10 (dd, 1 H, J=7.2, 8.8 Hz), 3.47-3.56 (m, 1 H), 2.80-2.89 (m, 1 H), 1.05 (t, 3 H, J=7.2 Hz). MS(ES) [M+H]$^+$ calad for C$_{11}$H$_{13}$NO$_2$, 192.1; found 192.2.

Compound 52: Preparation of(R)-4-phenyl-3-(prop-2-yn-1-yl)oxazolidin-2-one

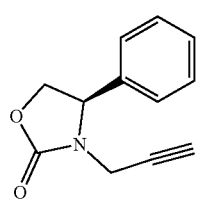

The titled compound 52 was prepared in 46% yield from (R)-4-phenyloxazolidin-2-one (80 mg) and 3-bromoprop-1-yne (116 mg) according to the procedure outlined for compound 51. $^1$HNMR (CDCl$_3$, 400 MHz): δ7.37-7.46 (m, 3 H), 7.32-7.35 (m, 2 H), 4.96 (t, 1 H, J=8.4 Hz), 4.67 (t, 1 H, J=8.4 Hz), 4.41 (dd, 1 H, J=2.4, 17.6 Hz), 4.16 (dd, 1 H, J=8.4, 8.4 Hz), 3.39 (dd, 1 H, J=2.4, 17.6 Hz), 2.25 (t, 1 H, J=2.4 Hz). LC-MS (ESI) [M+H]$^+$ calad for C$_{12}$H$_{11}$NO$_2$, 202.1; found, 202.2.

Compound 53 and 54

Compound 53 and 54 are prepared according to the procedure outlined in scheme 1

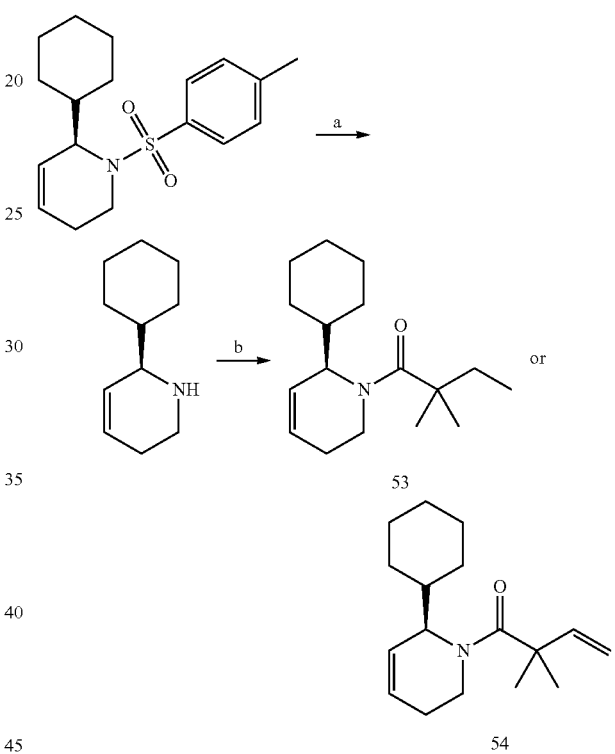

Scheme 1: reagent and conditions: (a) Na/THF, −78° C. (b) NaH, 2,2-dimethylbutanoyl chloride(for 53) or 2,2-dimethylbut-3-enoyl chloride (for 54), THF.

Compound 56 and 57

Compound 56 and 57 are prepared according to the procedure outlined in scheme 2

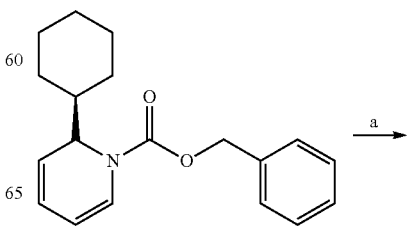

-continued

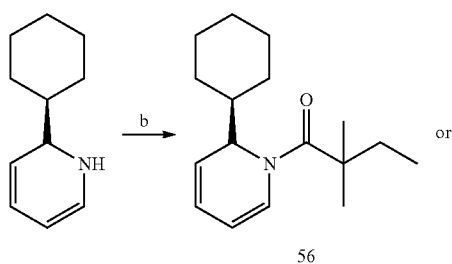

56

Compound 59-68

Compound 59-68 are prepared according to the procedure outlined in scheme 4

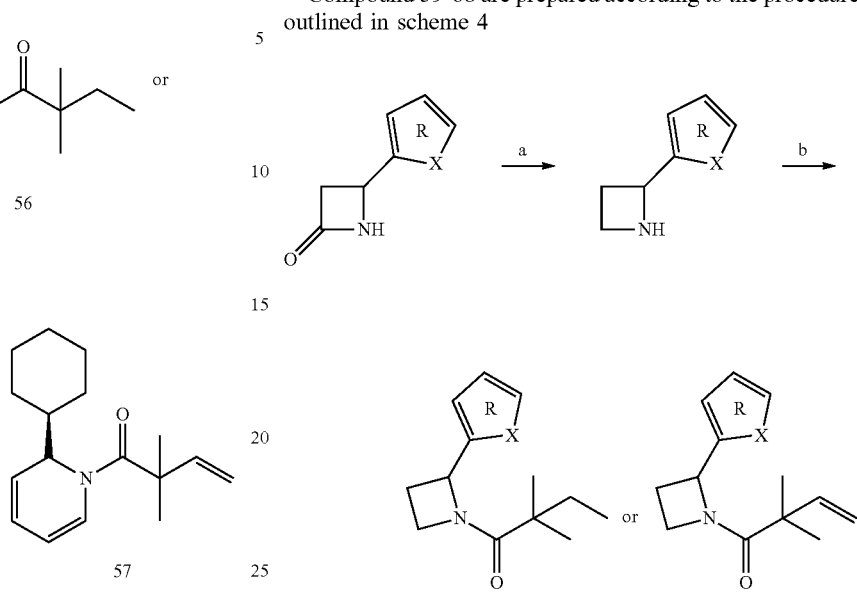

Scheme 2: reagent and conditions: (a) Pd/C, H$_2$ (b) NaH, 2,2-dimethylbutanoyl chloride (for 56) or 2,2-dimethylbut-3-enoyl chloride (for 57), THF.

Scheme 4: reagent and conditions: (a) LiAlH$_4$, THF, reflux (b) Et$_3$N, 2,2-dimethylbutanoyl chloride (for 59-61, 65, 67) or 2,2-dimethylbut-3-enoyl chloride (62-64, 66, 68) THF.

Compound 55 and 58

Compound 55 and 58 are prepared according to the procedure outlined in scheme 3

Compound 69

Compound 69 are prepared according to the procedure outlined in scheme 5

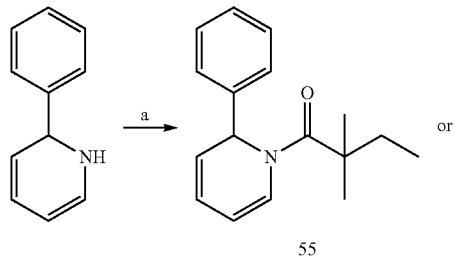

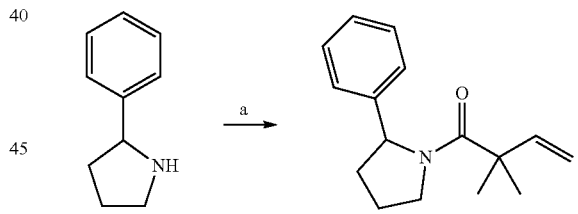

Scheme 5: reagent and conditions: (a) Et$_3$N, 2,2-dimethylbut-3-enoyl chloride, THF.

Compound 70

Compound 70 is prepared according to the procedure of scheme 6

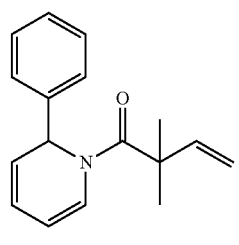

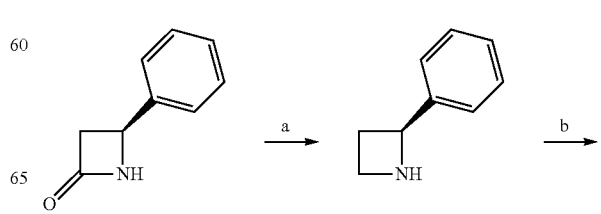

Scheme 3: reagent and conditions: (a) NaH, 2,2-dimethylbutanoyl chloride (for 55) or 2,2-dimethylbut-3-enoyl chloride (for 58), THF.

-continued

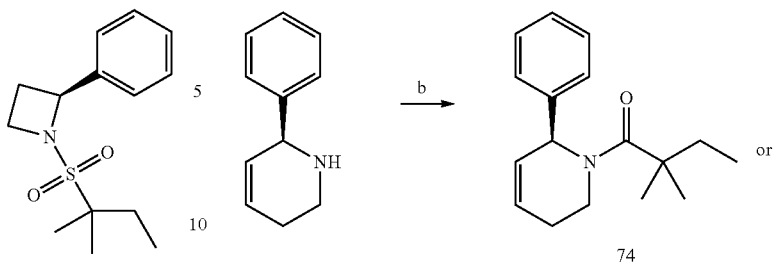

Scheme 6: reagent and conditions: (a) LiAlH₄, THF, reflux (b) Et₃N, 2-methylbutane-2-sulfonyl chloride, THF.

Compound 72 and 73

Compound 72 and 73 are prepared according to the procedure of scheme 7

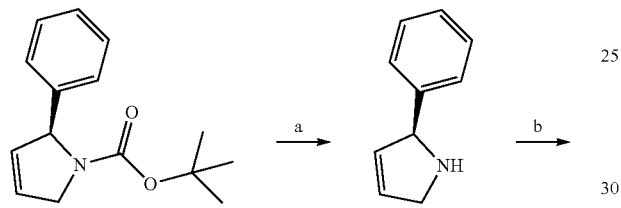

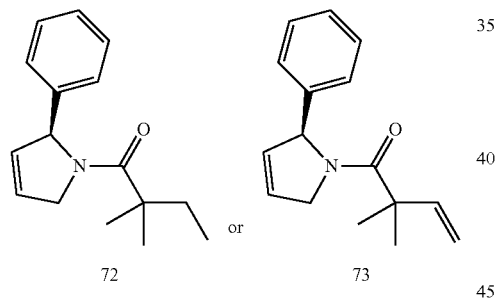

Scheme 7: reagent and conditions: (a) TFA/DCM (b) Et₃N, 2,2-dimethylbutanoyl chloride (for 72) or 2,2-dimethylbut-3-enoyl chloride (for 73), THF.

Compound 74 and 75

Compound 74 and 75 are prepared according to the procedure of scheme 8

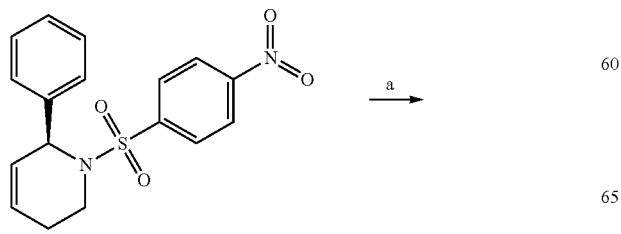

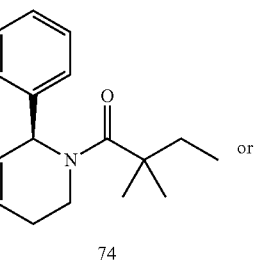

74

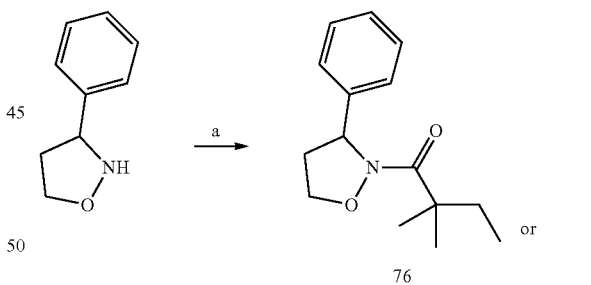

75

Scheme 8: reagent and conditions: (a) K₂CO₃, thiophenol, DMF (b) Et₃N, 2,2-dimethylbutanoyl chloride (for 74) or 2,2-dimethylbut-3-enoyl chloride (for 75), THF.

Compound 76 and 77

Compound 76 and 77 are prepared according to the procedure of scheme 9

76

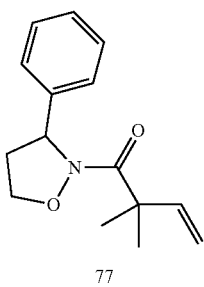

77

Scheme 9: reagent and conditions: (a) Et₃N, 2,2-dimethylbutanoyl chloride (for 76) or 2,2-dimethylbut-3-enoyl chloride (for 77), THF.

Compound 78: Preparation of 2,2-dimethyl-1-(2-phenyl-1H-pyrrol-1-yl)butan-1-one

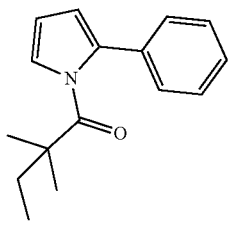 [SMILES: CCC(C)(C)C(=O)n1cccc1-c1ccccc1]

To a stirred suspension of NaH (30 mg, 0.7 mmol) in dry THF (3 ml) was added a solution of 2-phenyl-1H-pyrrole (50 mg) in dry THF (1 mll), under an argon atmosphere. After stirring at rt for 5 min, hydrogen evolution ceased and 2,2-dimethylbutanoyl chloride (56 mg) was added. The reaction mixture was stirred at rt for 1 h. The reaction mixture was poured onto saturated aqueous NH$_4$Cl, which was extracted with CH2Cl2 (3.x.10 ml). The combined organic layers were dried over Na$_2$SO$_4$ and evaporated to yield the desired product (30 mg, 36%). $^1$HNMR (CDCl$_3$, 400 MHz): δ 7.45-7.47 (m, 2H), 7.34-7.39 (m, 2H), 7.18-7.23 (m, 1H), 6.85-6.88 (d, 1H, J=8.0 Hz), 6.51-6.54 (m, 1H), 6.29-6.32 (d, 1H, J=8.0 Hz), 1.39 (q, 2 H, J=7.6 Hz), 0.97 (s, 6 H), 0.86 (t, 3 H, J=7.6 Hz). LC-MS (ESI) [M+H]$^+$ calad for C$_{16}$H$_{19}$NO, 242.1; found, 242.4.

Compound S1: Preparation of 1-((2R,3S)-3-hydroxy-2-phenylpyrrolidin-1-yl)-2,2-dimethylbutan-1-one

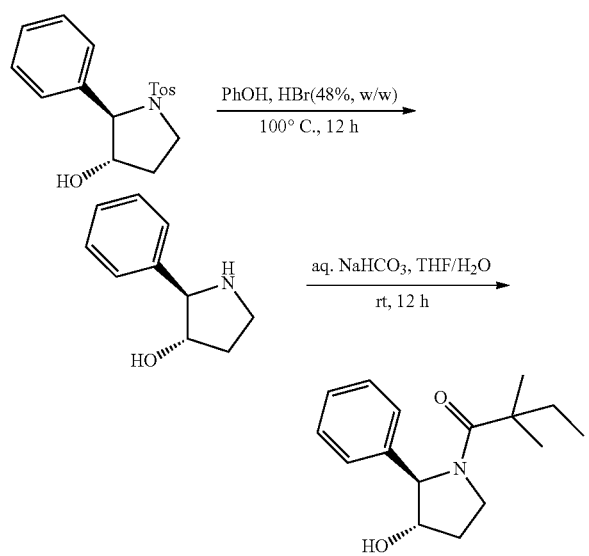

(2R,3S)-2-phenyl-1-tosylpyrrolidin-3-ol was prepared according to methods previously described (US2009/0012120A1) (35 mg) and phenol (31 mg) were added in 4 mL of HBr(48%, w/w). The mixture was strried at 100° C. for 12 h and then cooled to room temperature, extracted with ether (2 mL) and the ether layer was discarded. The aqueous was freeze-dried to give (2R,3S)-2-phenylpyrrolidin-3-ol (30 mg) without further purification.

The above amino-alcohol compound (30 mg) dissolved in 2 mL of THF/H$_2$O (1:1) and 0.45 mL of saturated aqueous NaHCO$_3$. The solution was cooled to 0° C. and 2,2-dimethylbutanoylchloride (16 mg) was added and the mixture was stirred at room temperature for 12 h. The mixture was extracted with EtOAc and the combined organic layer washed with brine, dried (Na$_2$SO$_4$) and concentrated in vacuo. Purification by pre-HPLC to give compound S1 (15 mg, 52% in two steps) as a colorlesss oil. $^1$H NMR (400 MHz, CDCl$_3$) δ 7.30 (t, J=7.3 Hz, 2H), 7.22 (t, J=7.0 Hz, 1H), 7.12 (d, J=7.4 Hz, 2H), 5.33 (brs, 1H), 4.19 (brs, 1H), 4.05-3.94(m, 2H), 2.05 (brs, 1H), 1.91 (brs, 1H), 1.73-1.60 (m, 2H), 1.25 (s, 3H), 1.20 (s, 3H), 0.88 (t, J=6.8 Hz, 3H). LC-MS (ESI) [M+H]$^+$ calad for C$_{16}$H$_{24}$NO$_2$, 262.18; found, 262.44.

Compound S2: Preparation of 1-((2R,3R)-3-hydroxy-2-phenylpyrrolidin-1-yl)-2,2-dimethylbutan-1-one

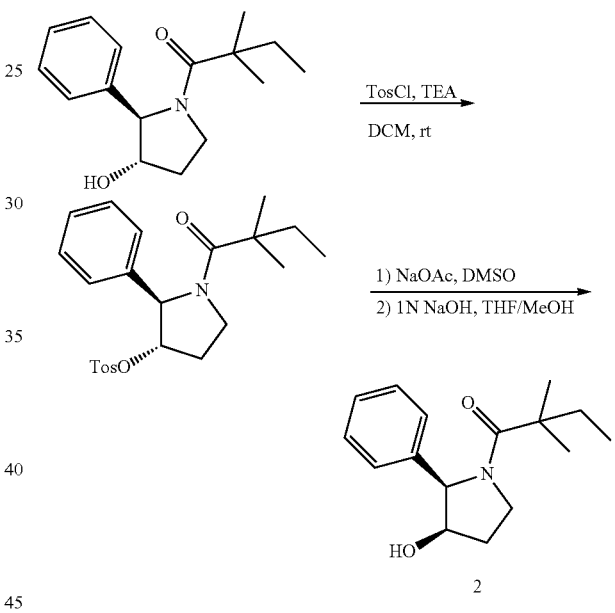

To a solution of compound S1 (30 mg) in dry DCM (4 mL) was added 4-toluene sulfonyl chloride (27 mg) and the mixture was stirred at room temperature for 16 h and quenched with water (2 mL). The aqueous layers were extracted with DCM (15 mL×3) and the organic layers was combined, washed with brine, dried with Na$_2$SO$_4$ and evaporated to dryness. The residue was purified by column chromatography to give (2R,3S)-1-(2,2-dimethylbutanoyl)-2-phenylpyrrolidin-3-yl-4-methylbenzenesulfonate (36 mg, 75%). LC-MS (ESI) [M+H]$^+$ calad for C$_{23}$H$_{30}$NO$_4$S, 416.19; found, 416.52.

The above intermediate was dissolved in dry DMSO (2 mL) and sodium acetate trihydrate (12 mg) was added. The mixture was stirred at 100° C. for 60 h and 4 mL of water was added. The aqueous layers were extracted with DCM (15 mL×3) and the organic layers was combined, washed with brine, dried with Na$_2$SO$_4$ and evaporated to dryness. The residue was used for next step without further purification. The above intermediate (15 mg) was dissolved in THF (1 mL) and MeOH (0.2 mL) and 0.01 mL 1N NaOH was added. The mixture was stirred at 0° C. for 1 h andneutralized with 1N HCl. The aqueous layers were extracted with DCM and the organic layers was combined and evaporated to dryness. The residue was purified by Pre-TLC to give the titled compound S2 (5 mg, 17%, in three steps). $^1$H NMR (400 MHz, CDCl$_3$) δ 7.33 (t, J=7.2 Hz, 2H), 7.27-7.24 (m, 1H), 7.15 (d, J=7.8 Hz, 2H), 5.18 (d, J=4.5 Hz, 1H), 3.93 (brs, 2H), 2.08 (brs, 1H), 1.71 (brs, 1H), 1.62-1.53 (m, 2H), 1.19 (s, 6H), 0.85 (t, J=6.8 Hz, 3H). LC-MS (ESI) [M+H]$^+$ calad for C$_{16}$H$_{24}$NO$_2$, 262.18; found, 262.44.

Compound S3: Preparation of (R)-1-(2,2-dimethylbutanoyl)-2-phenylpyrrolidin-3-one

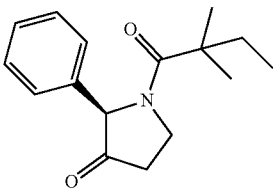 [SMILES: CCC(C)(C)C(=O)N1CCC(=O)[C@H]1c1ccccc1]

To a mixture of compound S2 (6 mg) and 4A MS (10 mg) in DCM (2 mL) was added PCC (15 mg) at 0° C. The mixture was stirred for 1 hour at room temperature, followed by filtering through a pad of Al$_2$O$_3$. The filtrate was concentrated in vacuo. The resulting residue was purified by pre-TLC to afford the desired product S3 (4 mg, 67%). $^1$H NMR (400 MHz, CDCl$_3$) δ 7.38-7.21 (m, 5H), 4.50-4.41 (m, 1H), 4.07-3.98 (m, 1H), 2.75-2.62 (m, 2H), 1.72-1.59 (m, 2H), 1.22 (d, J=15.1 Hz, 6H), 0.85 (t, J=7.3 Hz, 3H). LC-MS (ESI) [M+H]$^+$ calad for C$_{16}$H$_{22}$NO$_2$, 260.16; found, 262.30.

Synthetic Route for Compound S4 and S5

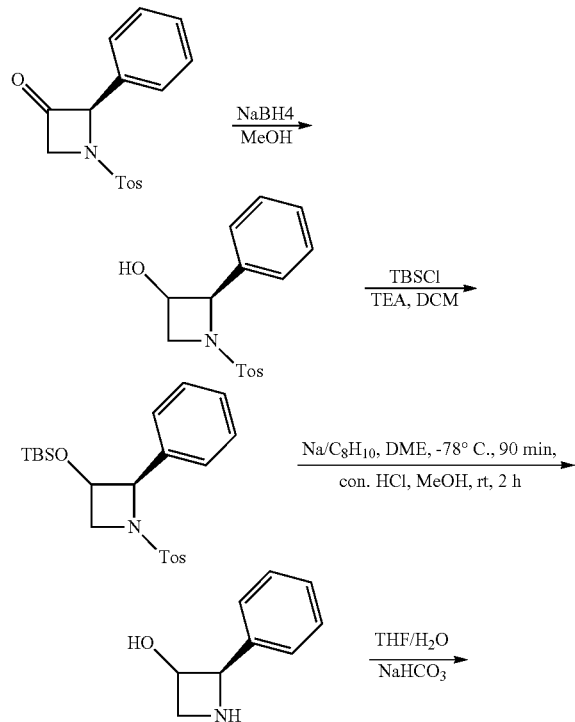

Compound S4: Preparation of 1-((2R,3R)-3-hydroxy-2-phenylazetidin-1-yl)-2,2-dimethylbutan-1-one

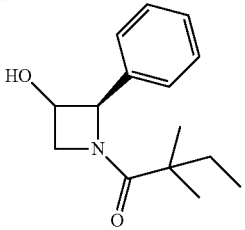

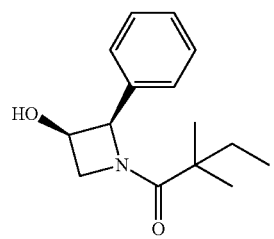 [SMILES: CCC(C)(C)C(=O)N1C[C@@H](O)[C@H]1c1ccccc1]

(R)-2-phenyl-1-tosylazetidin-3-one was prepared according to methods previously described (Tetrahedron 2008, 64, 9928-9936) and NaBH4 (75.5 mg) in methanol (15 mL) were stirred at room temperature for 3 h. The reaction mixture was quenched by addition of solid citric acid until pH reached 5 to 6. To the reaction mixture was added silica gel and the solvent was distilled off. The residue was purified by column chromatography on silica gel (EtOAc: hexane, 1:3) to afford the desired products, two isomers a and b, and its absolute configuration was confirmed by $^1$H-$^1$H nuclear overhauser effects (NOE). Product a: 1-((2R,3R)-3-hydroxy-2-phenylazetidin-1-yl)-2,2-dimethylbutan-1-one, $^1$H NMR (400 MHz, CDCl$_3$) δ 7.72 (d, J=8.3 Hz, 2H), 7.44-7.31 (m, 7H), 5.11 (d, J=6.7 Hz, 1H), 4.37 (td, J=6.7, 2.8 Hz, 1H), 4.05 (dd, J=9.5, 6.6 Hz, 1H), 3.74 (ddd, J=9.5, 2.8, 1.1 Hz, 1H), 2.45 (s, 3H). Product b: 1-((2R,3S)-3-hydroxy-2-phenylazetidin-1-yl)-2,2-dimethylbutan-1-one, $^1$H NMR (400 MHz, CDCl$_3$) δ 7.66 (d, J=8.2 Hz, 2H), 7.41-7.28 (m, 7H), 4.50 (d, J=5.7 Hz, 1H), 4.24 (dd, J=12.5, 6.4 Hz, 1H), 4.02 (t, J=7.3 Hz, 1H), 3.52-3.45 (m, 1H), 2.44 (s, 3H).

1-((2R,3R)-3-hydroxy-2-phenylazetidin-1-yl)-2,2-dimethylbutan-1-one (50 mg) and triethylamine (33.2 mg) were dissolved in 2mL of DCM, and 34 mg of p-toluenesulfonyl chloride was added at 0° C. The mixture was allowed to stir at room temperature for 12 h, and then concentrated in vacuo. The residue was purified by column chromatography on silica gel (EtOAc: hexane, 1:5) to afford (2R,3R)-3-((tert-butyldimethylsilyl)oxy)-2-phenyl-1-tosylazetidine (63 mg, 92%). $^1$H NMR (400 MHz, cdcl$_3$) δ 7.68 (d, J=8.3 Hz, 2H), 7.38-7.26 (m, 7H), 4.99 (d, J=6.6 Hz, 1H), 4.38 (td, J=6.5, 2.7 Hz, 1H), 4.04 (dd, J=8.9, 6.4 Hz, 1H), 3.69 (ddd, J=8.9, 2.7, 1.0 Hz, 1H), 2.43 (s, 3H), 0.63 (s, 9H), −0.19 (s, 3H), −0.42 (s, 3H).

To a solution of (2R,3R)-3-((tert-butyldimethylsilyl)oxy)-2-phenyl-1-tosylazetidine (30 mg) in absolute 1,2-dimethoxyethane (6 mL) was added dropwise the prepared sodium naphthalene (0.67 M, 1.2 mL) at −78° C. The reaction mixture was stirred for 90 min, diluted with water and extracted with chloroform. The combined organic layer was washed with saturated brine, and concentrated to afford the crude (2R,3R)-3-((tert-butyldimethylsilyl)oxy)-2-phenylazetidine (45 mg), which was dissolved in methanol (4 mL), and added concentrated hydrochloric acid (0.2 mL). The mixture was stirred for 2 h, and added saturated NaHCO₃ solution until pH reached 8. The mixture was concentrated in vacuo, and the residue was diluted with DCM and water, the aqueous was extracted with DCM, the combined organic layer was washed with saturated brine, and concentrated to afford crude product, (2R,3R)-2-phenylazetidin-3-ol(32 mg), which was used for next step without further purification.

To a solution of (2R,3R)-2-phenylazetidin-3-ol (32 mg) in THF (2 mL) and H₂O (2 mL) was added sat. NaHCO₃ (0.5 mL). The mixture was cooled to 0° C., and 2,2-dimethylbutanoyl chloride (29 mg) was added and stirred at room temperature for overnight. The mixture was extracted with DCM and the combined organic layers were washed with water and concentrated. The crude product was purified by Pre-HPLC to give compound S4 (6.8 mg, 36% in three steps). ¹H NMR (400 MHz, CDCl₃) δ 7.39-7.22 (m, 5H), 5.12 (d, J=3.4 Hz, 1H), 4.62-4.53 (m, 1H), 4.31 (dd, J=10.3, 3.9 Hz, 1H), 4.14 (dd, J=9.4, 4.5 Hz, 1H), 1.56-1.52 (m, 2H), 1.16 (d, J=2.4 Hz, 6H), 0.88 (t, J=7.5 Hz, 3H). LC-MS (ESI) [M+H]+ calad for $C_{15}H_{22}NO_2$, 248.16, found, 248.25

Compound S5: Preparation of 1-((2R,3S)-3-hydroxy-2-phenylazetidin-1-yl)-2,2-dimethylbutan-1-one

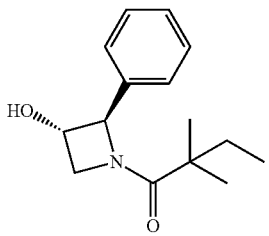 [SMILES: CCC(C)(C)C(=O)N1C[C@H](O)[C@H]1c1ccccc1]

Compound S5 was prepared from 1-((2R,3S)-3-hydroxy-2-phenylazetidin-1-yl)-2,2-dimethylbutan-1-one according to the procedure outlined for compound S4. ¹H NMR (400 MHz, CDCl₃) δ 7.43-7.22 (m, 5H), 4.76-4.71 (m, 1H), 4.65-4.58 (m, 1H), 4.16-4.09 (m, 1H), 3.72-3.65 (m, 1H), 1.54-1.52 (m, 2H), 1.23 (s, 6H), 0.86 (t, J=6.8 Hz, 3H). LC-MS (ESI) [M+H]+ calad for $C_{15}H_{22}NO_2$, 248.16, found, 248.25.

Compound S6: Preparation of (S)-1-(ethylsulfonyl)-2-phenylazetidine

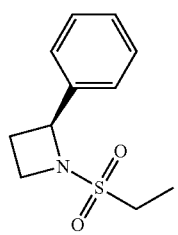

(S)-2-phenylazetidine (35 mg, 0.263 mmol) and triethylamine (53.2 mg, 0.526 mmol) were dissolved in 2 mL of dry CH₂Cl₂. Ethanesulfonyl chloride (40.4 mg, 0.316 mmol) was added slowly to the solution at 0° C. under nitrogen. The mixture was stirred at room temperature for 2 h, diluted with CH₂Cl₂ and water. The organic layer were washed with saturated NaHCO₃ solution, brine, dried with Na₂SO₄ and concentrated. The residue was purified by chromatography to give compound S6 (20 mg, 33%) as an light yellow oil. ¹H NMR (400 MHz, CDCl₃) δ 7.40-7.27 (m, 5H), 5.01 (dd, J=9.0, 5.5 Hz, 1H), 3.32 (dd, J=13.2, 6.4 Hz, 2H), 3.08-3.02 (m, 2H), 2.32 (m, 2H), 1.37 (t, J=7.4 Hz, 3H). LC-MS (ESI) [M+H]+ calad for $C_{11}H_{16}NO_2S$, 226.09; found, 226.21.

Compound S7: Preparation of (2S)-1-(tert-butylsulfinyl)-2-phenylazetidine

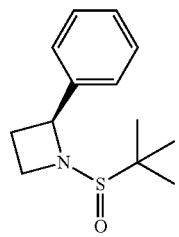 [SMILES: CC(C)(C)S(=O)N1CC[C@H]1c1ccccc1]

Compound S7 was prepared in 47% yield from (S)-2-phenylazetidine (55 mg) and 2-methylpropane-2-sulfinic chloride(69.4 mg)according to procedure outlined for compound S6. ¹H NMR (400 MHz, CDCl₃) δ 7.47 (d, J=8.0 Hz, 2H), 7.37-7.31 (m, 2H), 7.28-7.23 (m, 1H), 5.43-5.33 (t, J=8.0 Hz, 1H), 3.98 (dd, J=17.4, 8.0 Hz, 1H), 3.89-3.79 (m, 1H), 2.74-2.65 (m, 1H), 2.37-2.20 (m, 1H), 0.90 (s, 9H). LC-MS (ESI) [M+H]⁺ calad for $C_{13}H_{20}NOS$, 238.13; found, 238.28.

Compound S8: Preparation of (S)-1-(tert-butylsulfonyl)-2-phenylazetidine

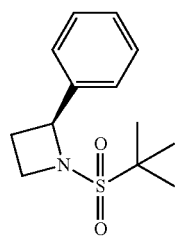 [SMILES: CC(C)(C)S(=O)(=O)N1CC[C@H]1c1ccccc1]

To a solution of compound S7(11 mg) in DCM (4 mL) was added m-CPBA (75%, w/w, 16 mg) at 0° C. The mixture was stirred at room temperature for 12 h, and concentrated in vacuo. The residue was purified by pre-TLC to give compound S8. ¹H NMR (400 MHz, cdcl₃) δ 7.49 (d, J=8.0 Hz, 2H), 7.39-7.33 (m, 2H), 7.30-7.25 (m, 1H), 5.45-5.35 (m, 1H), 4.00 (dd, J=17.4, 8.0 Hz, 1H), 3.91-3.81 (m, 1H), 2.76-2.68 (m, 1H), 2.39-2.22 (m, 1H), 0.92 (s, 9H).

Compound S9: Preparation of (S)-1-(tert-butylsulfonyl)-2-phenylazetidine

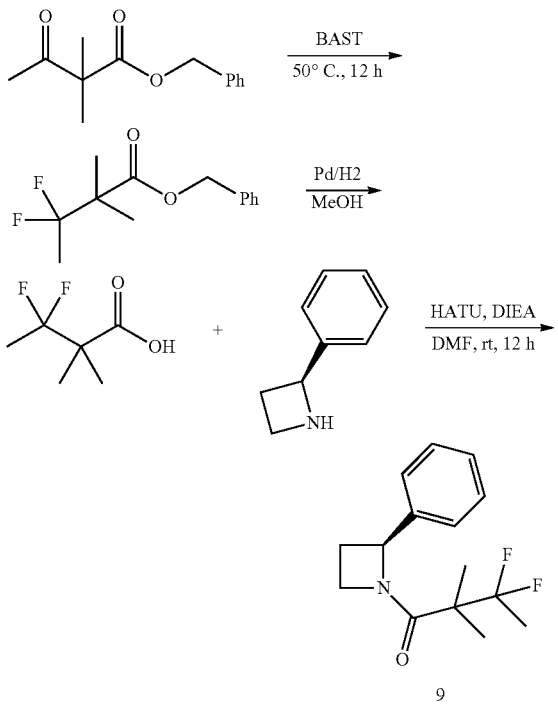

9

A mixture of benzyl 2,2-dimethyl-3-oxobutanoate (400 mg), bis(2-methoxyethyl) aminosulfur trifluoride (5 mL) and a drop of ethanol was stirred at 50° C. for 12 h. The mixture was cooled to 0° C., and cold water was added. The mixture was added saturated $NaHCO_3$ solution until pH reached 8, extracted with DCM. The combined organic layer washed with brine, dried ($Na_2SO_4$) and concentrated in vacuo. Purification by chromatography to benzyl 3,3-difluoro-2,2-dimethylbutanoate (206 mg, 47%). $^1$H NMR (400 MHz, $CDCl_3$) δ 7.38-7.30 (m, 5H), 5.15 (s, 2H), 1.63 (t, J=19.2 Hz, 3H), 1.34 (t, J=0.9 Hz, 6H).

To a stirred solution of benzyl 3,3-difluoro-2,2-dimethylbutanoate (206 mg) in methanol (5 mL) was added Pd/C (10%, 20.6 mg) and the resulting mixture was subjected to hydrogenation under 1 atm pressure for 12 h at room temperature. The mixture was filtered through celite pad and the filter cake was washed with methanol. The filtrate was evaporated under reduced pressure to give 3,3-difluoro-2,2-dimethyl butanoic acid (105 mg, 81%) as a white solid, which was used for next step without further purification. $^1$H NMR (400 MHz, $CDCl_3$) δ 1.73 (t, J=18 Hz, 3H), 1.38(s, 3H).

To a solution of (S)-2-phenylazetidine (70 mg) and 3,3-difluoro-2,2-dimethylbutanoic acid (40 mg) in dry DMF (1 mL) was added 2-(7-Aza-1H-benzotriazole-1-yl)-1,1,3,3-tetramethyluronium hexafluorophosphate (150 mg) and DIEA (0.14 mL). The mixture was stirred at room temperature for 12 h and concentrated in vacuo. The residue was diluted with $CH_2Cl_2$ and water. The aqueous layer was extracted with $CH_2Cl_2$. The organic layer were washed with saturated brine, dried with $Na_2SO_4$ and concentrated.

The residue was purified by pre-TLC to give compound S9 (35 mg, 50%). $^1$H NMR (400 MHz, $CDCl_3$) δ 7.38-7.22 (m, 5H), 5.39-5.31 (m, 1H), 4.59-4.45 (m, 2H), 2.73-2.65 (m, 1H), 2.16-2.06 (m, 1H), 1.59 (t, J=19.5 Hz, 3H), 1.32 (s, 6H). LC-MS (ESI) [M+H]$^+$ calad for $C_{15}H_{20}F_2NO$, 268.15; found, 268.19.

Compound S10: Preparation of 3,3-difluoro-2,2-dimethyl-1-(2-phenylpyrrolidin-1-yl) butan-1-one

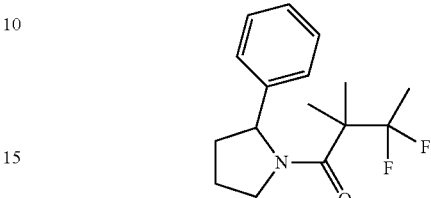

Compound S10 was prepared in 65% yield from 2-phenylpyrrolidine(48 mg) and 3,3-difluoro-2,2-dimethylbutanoic acid (50 mg) according to procedure outlined for compound S9. $^1$H NMR (400 MHz, $CDCl_3$) δ 7.29-7.09 (m, 5H), 5.30-5.13 (m, 1H), 3.95 (m, 2H), 2.25-2.16 (m, 1H), 2.09-1.68 (m, 3H), 1.54 (t, J=19.5 Hz, 3H), 1.39 (s, 6H). LC-MS (ESI) [M+H]$^+$ calad for $C_{16}H_{22}F_2NO$, 282.17; found, 282.36.

Compound S11: Preparation of 2,2-dimethyl-1-(2-phenylpyrrolidin-1-yl)propan-1-one

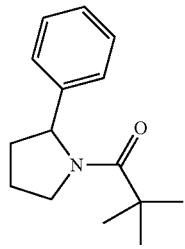 [SMILES: CC(C)(C)C(=O)N1CCCC1c1ccccc1]

Compound S11 was prepared in 74% yield from 2-phenylpyrrolidine (51 mg) and pivaloyl chloride (50 mg) according to procedure outlined for compound S6. $^1$H NMR (400 MHz, $CDCl_3$) δ 7.29-7.25 (m, 2H), 7.12-7.10 (m, 3H), 5.31-5.16 (m, 1H), 3.88-3.74 (m, 2H), 2.26-2.17 (m, 1H), 1.88-1.77 (m, 3H), 1.24 (s, 9H). LC-MS (ESI) [M+H]$^+$ calad for $C_{15}H_{22}NO$, 232.17; found, 232.20.

Compound S12: Preparation of (S)-2,2-dimethyl-1-(2-phenylazetidin-1-yl)propan-1-one

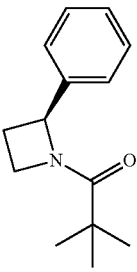 [SMILES: CC(C)(C)C(=O)N1CC[C@H]1c1ccccc1]

Compound S12 was prepared in 44% yield from (S)-2-phenylazetidine (10 mg) and pivaloyl chloride (13.5 mg) according to procedure outlined for compound S6. $^1$H NMR (400 MHz, CDCl$_3$) δ 7.37-7.31 (m, 2H), 7.28-7.25 (m, 3H), 5.14-5.05 (m, 1H), 4.08-3.98 (m, 2H), 2.20-2.08 (m, 2H), 1.20 (s, 9H). LC-MS (ESI) [M+H]$^+$ calad for C$_{14}$H$_{20}$NO, 218.15; found, 218.20.

Compound S13

Compound S13 is prepared according to the procedure outlined in scheme 1

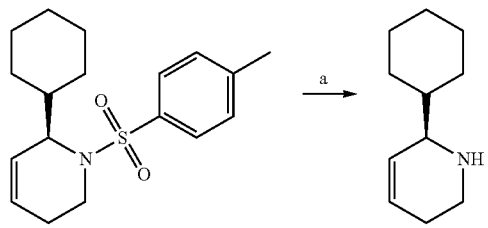

Scheme 1: reagent and conditions: (a) Na/THF, −78° C. (b) 3,3-difluoro-2,2-dimethyl butanoic acid, EDCI, DIEA, DMF, rt.

Compound S14:

Compound S14 is prepared according to the procedure outlined in scheme 2

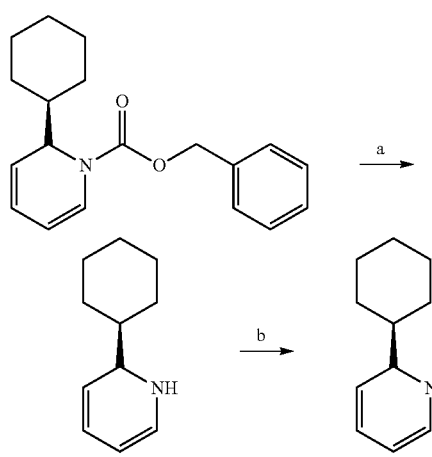

Scheme 2: reagent and conditions: (a) Pd/C, H$_2$ (b) 3,3-difluoro-2,2-dimethylbutanoyl chloride, NaH, THF.

Compound S15

Compound S15 is prepared according to the procedure outlined in scheme 3

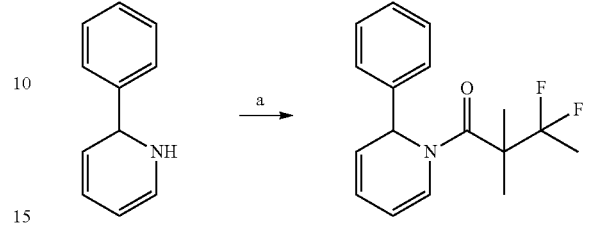

Scheme 3: reagent and conditions: (a) 3,3-difluoro-2,2-dimethylbutanoyl chloride, NaH, THF.

Compound S16

Compound S16 is prepared according to the procedure outlined in scheme 4

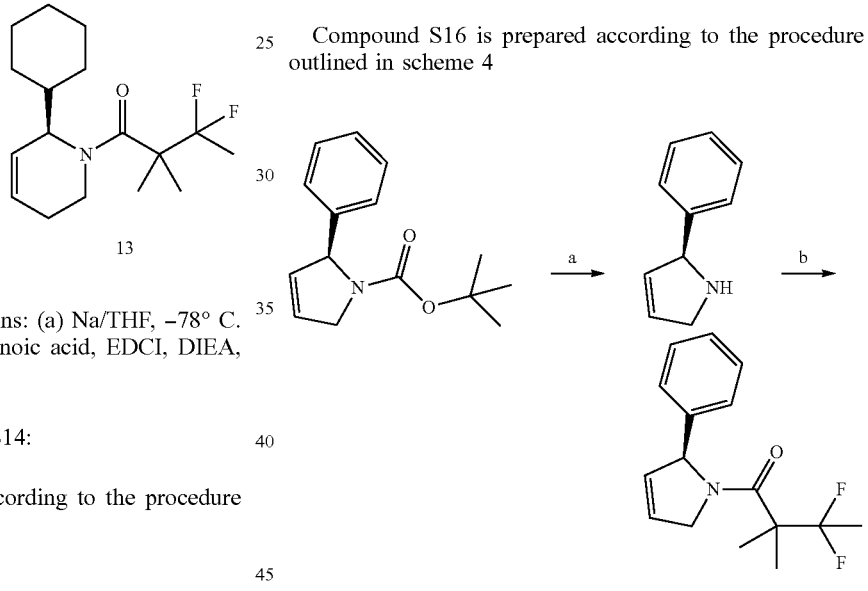

Scheme 4: reagent and conditions: (a) TFA/DCM (b) 3,3-difluoro-2,2-dimethylbutanoyl chloride, Et$_3$N, DCM.

Compound S17

Compound S17 is prepared according to the procedure outlined in scheme 5

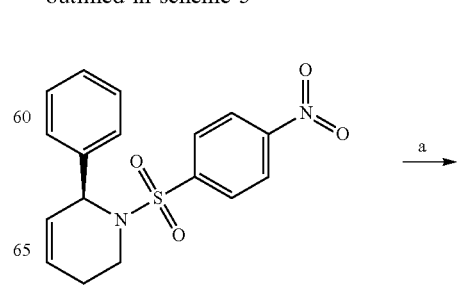

-continued

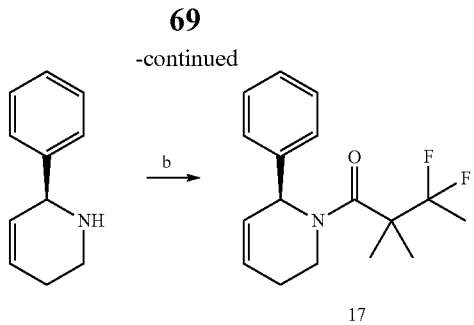

Scheme 5: reagent and conditions: (a) K₂CO₃, thiophenol, DMF (b) 3,3-difluoro-2,2 dimethylbutanoyl chloride, Et₃N, DCM.

3. Kinase Assay of RIPK1

Materials: Recombinant full-length RIPK1 protein with N-terminal GST-tag (Cat # R07-34G) was purchased from SignalChem. The ADP-Glo™ kinase assay kit (Cat # V9102) was from Promega. MBP (cat # M2295) protein and all the other chemicals were from Sigma. The 384-well assay plates (Cat #3674, white, opaque) were purchased from Corning.

Kinase activity assay and data analysis: The RIPK1 kinase assay was performed in white 384-well plate. The assay buffer contained 25 mM HEPES (pH 7.2), 20 mM MgCl2, 12.5 mM MnCl2, 5 mM EGTA, 2 mM EDTA, 12.5 mM β-glycerol phosphate and 2 mM DTT. RIPK1 was first incubated with compounds or DMSO control for 15 min, then ATP/MBP substrate mixture was added to initiate the reaction. The final concentration of RIPK1 was 161 nM, while the final concentration of ATP was 50 uM, and MBP 20 uM. After 90 min reaction at room temperature, the ADP-Glo reagent and detection solution were added following the technical manual of ADP-Glo™ kinase assay kit (Promega). The luminescence was measured on PerkinElmer Enspire. The data was analyzed using Graphpad Prism (GraphPad Software; www.graphpad.com). The curves were fitted using a non-linear regression model with a sigmoidal dose response.

Results: pIC50 of hRIP1 kinase assay correlated with our pIC50 of cell necrosis assay. Exemplary data are shown below:

| # | RIP1 CMPD ID | Cell viability assay, EC50 ( nM) | hRIP1 kinase assay, IC50(nM) or % inhibition at 2 uM |
|---|---|---|---|
| 10 | TC001124 | 9.882 | IC50 = 22.5 nM |
| 2 | TC001129 | 29.64 | IC50 = 34.8 nM |
| 25 | TC001273 | 555.6 | IC50 = 152 nM |
| 38 | TC001262 | 8.39 | IC50 = 13.7 nM |
| 15 | TC001287 | 396 | IC50 = 460 nM |
| 24 | TC001207 | 7 | IC50 = 19.8 nM |
| 31 | TC001265 | 609.4 | IC50 = 1065 nM |
| 13 | TC001252 | 2615 | 69% inhibition at 2 uM |

4. Necrosis Assay

Methods:

HT-29 cells were cultured in McCoy's 5A culture medium (Invitrogen). On day one, HT-29 cells were plated in 96-well assay plates at density of 2,500-3,500 cells per well. On day two, necrosis were induced by adding 20 ng/ml TNF-α (T), 10 0nM Smac mimetic (S), and 20 mM z-VAD (Z). At the same time, 10 mM compound from a chemical library of ~200,000 compounds was delivered into each well. After 24 hrs treatment, cell viability was determined by measuring ATP level using the CellTiter-Glo Luminescent Cell Viability Assay kit. A CellTiter-Glo Assay (Promega) was performed according to the manufacturer's instructions Luminescence was recorded with a PerkinElmer EnSpire Multimode Plate Reader. Survived cells were normalized to those cells treated with DMSO. Nec-1 was used as a positive control for screening necrosis inhibitors. Data are represented as mean±standard deviation of duplicates Dose-dependent inhibition of necrosis by compound #9 and the derivative compounds in HT-29 cells were determined by measuring ATP levels as described above. Compound necrosis activity data are reported below:

| # | EC50 | # | EC50 | # | EC50 |
|---|---|---|---|---|---|
| 1 | 1-100 uM | 27 | 1-1000 nM | 53 | 1-1000 uM |
| 2 | 1-1000 nM | 28 | 1-10 uM | 54 | 1-1000 uM |
| 3 | 1-1000 nM | 29 | 1-100 uM | 55 | 1-1000 uM |
| 4 | 1-1000 nM | 30 | 1-10 uM | 56 | 1-1000 uM |
| 5 | 1-1000 nM | 31 | 1-1000 nM | 57 | 1-1000 uM |
| 6 | 1-100 uM | 32 | 1-1000 nM | 58 | 1-1000 uM |
| 7 | 1-100 uM | 33 | 1-100 uM | 59 | 1-1000 uM |
| 8 | 1-1000 uM | 34 | 1-100 uM | 60 | 1-1000 uM |
| 9 | 1-1000 nM | 35 | 1-1000 nM | 61 | 1-1000 uM |
| 10 | 1-1000 nM | 36 | 1-1000 nM | 62 | 1-1000 uM |
| 11 | 1-100 uM | 37 | 1-100 uM | 63 | 1-1000 uM |
| 12 | 1-100 uM | 38 | 1-1000 nM | 64 | 1-1000 uM |
| 13 | 1-10 uM | 39 | 1-10 uM | 65 | 1-1000 uM |
| 14 | 1-1000 nM | 40 | 1-100 uM | 66 | 1-1000 uM |
| 15 | 1-1000 nM | 41 | 1-100 uM | 67 | 1-1000 uM |
| 16 | 1-10 uM | 42 | 1-100 uM | 68 | 1-1000 uM |
| 17 | 1-100 uM | 43 | 1-100 uM | 69 | 1-1000 uM |
| 18 | 1-100 uM | 44 | 1-10 uM | 70 | 1-1000 uM |
| 19 | 1-100 uM | 45 | 1-100 uM | 71 | 1-1000 uM |
| 20 | 1-1000 nM | 46 | 1-1000 nM | 72 | 1-1000 uM |
| 21 | 1-1000 nM | 47 | 1-10 uM | 73 | 1-1000 uM |
| 22 | 1-1000 nM | 48 | 1-100 uM | 74 | 1-1000 uM |
| 23 | 1-1000 nM | 49 | 1-100 uM | 75 | 1-1000 uM |
| 24 | 1-1000 nM | 50 | 1-100 uM | 76 | 1-1000 uM |
| 25 | 1-1000 nM | 51 | 1-100 uM | 77 | 1-1000 uM |
| 26 | 1-1000 nM | 52 | 1-100 uM | 78 | 1-100 uM |
| S1 | 1-10 uM | S2 | 1-100 uM | S3 | 1-10 uM |
| S4 | 1-10 uM | S5 | 1-100 uM | S6 | 1-100 uM |
| S7 | 1-10 uM | S8 | 1-100 uM | S9 | 1-1000 nM |
| S10 | 1-1000 nM | S11 | 1-1000 nM | S12 | 1-1000 uM |
| S13 | 1-100 uM | S14 | 1-100 uM | S15 | 1-100 uM |
| S16 | 1-100 uM | S17 | 1-100 uM | | |

What is claimed is:

1. A method of treating a necrosis-associated disease or condition, comprising administering an effective amount of a composition to a patient in need thereof, the composition comprising a compound, or a pharmaceutically acceptable salt, hydrate or stereoisomer of the compound or corresponding sulfonamide, and a pharmaceutically-acceptable excipient, in unit dosage, wherein the compound is an inhibitor of cellular necrosis and/or human receptor interacting protein 1 kinase (RIP1), of formula:

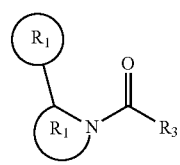

I wherein:
R₁ is (a) substituted or unsubstituted phenyl;
  (b) substituted or unsubstituted 2-, 3- or 4-pyridine;
  (c) substituted or unsubstituted naphthyl or 3-azanaphthyl;
  (d) substituted or unsubstituted 0-3 heteroatom cyclohexyl, cyclopentyl; or
  (e) substituted or unsubstituted 0-3 heteroatom cyclopentene or cyclopentadiene;
R₂ is substituted or unsubstituted aziridine, azetidine, pyrrolidine, piperidine, oxazridine, oxazetidine, oxazolidine, oxazinane, thiaziridine, thiazetidine, thiazolidine, thiazinane, diaziridine, diazetidine, diazolidine (pyrazolidine), diazinane; or
R₂ is substituted or unsubstituted pyrrole, dihydropyrrole, pyridine, dihydropyridine, tetrahydropyridine, azole, pyrimidine, oxazine, thiazine, triazine, ozadiazine, thiadiazine; and
R₃ is substituted or unsubstituted, 0-3 heteroatom C1-C9 alkyl, alkenyl, or alkynyl; or
a corresponding sulfonamide of the amide compound, or
a pharmaceutically acceptable salt, hydrate or stereoisomer the compound or corresponding sulfonamide.

2. The method of claim 1 wherein:
R₁ is substituted or unsubstituted: phenyl, cyclohexyl, furan, thiophene or azole.

3. The method of claim 1, wherein:
R₁ is substituted or unsubstituted: phenyl or cyclohexyl.

4. The method of claim 1, wherein:
R₁ is substituted or unsubstituted phenyl; or
a pharmaceutically acceptable salt, hydrate or stereoisomer of the compound or corresponding sulfonamide.

5. The method of claim 1, wherein:
R₁ is fluoro-substituted or unsubstituted phenyl.

6. The method of claim 1, wherein:
R₂ is substituted or unsubstituted: aziridine, azetidine, pyrrolidine, piperidine, oxazolidine, oxazinane; diazolidine, diazinane, pyrrole, dihydropyrrole, dihydropyridine, or tetrahydropyridine.

7. The method of claim 1, wherein:
R₂ is substituted or unsubstituted: azetidine, pyrrolidine, piperidine, oxazolidine, diazolidine, diazinane.

8. The method of claim 1, wherein:
R₂ is substituted or unsubstituted: azetidine or pyrrolidine.

9. The method of claim 1, wherein:
R₂ is unsubstituted: azetidine or pyrrolidine.

10. The method of claim 1 wherein:
R₂ is substituted azole.

11. The method of claim 1 wherein:
R₂ is substituted or unsubstituted azole that is a pyrazole, imidazole, triazole, tetrazole, pentazole, oxazole, isoxazole, thiazole or isothiazole.

12. The method of claim 1 wherein:
R₂ is substituted or unsubstituted azole that is a pyrazole, that is 2-pyrazole.

13. The method of claim 1 wherein:
R₂ is substituted or unsubstituted azole that is a pyrazole, that is 4,5-dihydro-1H-pyrazole.

14. The method of claim 1 wherein R₃ is substituted or unsubstituted, 0-3 heteroatom, cycloalkyl.

15. The method of claim 1, wherein:
R₁ is substituted or unsubstituted phenyl; and
R₂ is substituted azole.

16. The method of claim 1, wherein:
R₁ is fluoro-substituted or unsubstituted phenyl; and
R₂ is substituted azole.

17. The method of claim 1, wherein:
R₁ is substituted or unsubstituted phenyl; and
R₂ is substituted or unsubstituted azole that is a pyrazole, imidazole, triazole, tetrazole, pentazole, oxazole, isoxazole, thiazole or isothiazole.

18. The method of claim 1, wherein:
R₁ is fluoro-substituted or unsubstituted phenyl; and
R₂ is substituted or unsubstituted azole that is a pyrazole, imidazole, triazole, tetrazole, pentazole, oxazole, isoxazole, thiazole or isothiazole.

19. The method of claim 1, wherein:
R₁ is substituted or unsubstituted phenyl; and
R₂ is substituted or unsubstituted azole that is a pyrazole, that is 2-pyrazole.

20. The method of claim 1, wherein:
R₁ is fluoro-substituted or unsubstituted phenyl; and
R₂ is substituted or unsubstituted azole that is a pyrazole, that is 2-pyrazole.

21. The method of claim 1, wherein:
R₁ is substituted or unsubstituted phenyl; and
R₂ is substituted or unsubstituted azole that is a pyrazole, that is 4,5-dihydro-1H-pyrazole.

22. The method of claim 1, wherein:
R₁ is fluoro-substituted or unsubstituted phenyl; and
R₂ is substituted or unsubstituted azole that is a pyrazole, that is 4,5-dihydro-1H-pyrazole.

* * * * *